United States Patent [19]

Levorse et al.

[11] Patent Number: 5,389,608

[45] Date of Patent: Feb. 14, 1995

[54] 1-PHENYL-1-CYANO-$C_5$-$C_7$ ALKANES, ORGANOLEPTIC USES THEREOF AND PROCESS FOR PREPARING SAME

[75] Inventors: Anthony T. Levorse, South Amboy; Marie R. Hanna, Keyport; Charles E. J. Beck, Summit; Kathleen E. Boardwick, Keyport, all of N.J.

[73] Assignee: International Flavors & Fragrances Inc., New York, N.Y.

[21] Appl. No.: 241,725

[22] Filed: May 12, 1994

[51] Int. Cl.$^6$ .............................................. A61K 7/46
[52] U.S. Cl. .................................. 512/6; 252/174.11; 252/8.6
[58] Field of Search .................. 512/6; 558/373; 252/8.6, 174.11

[56] References Cited

U.S. PATENT DOCUMENTS

| | | | |
|---|---|---|---|
| 2,919,274 | 12/1959 | Faust et al. | 558/388 |
| 4,040,986 | 8/1977 | Boelens et al. | 512/6 |
| 4,459,224 | 7/1984 | Van der Weardt et al. | 512/6 |
| 5,177,250 | 1/1993 | Laurenyo | 558/388 |

FOREIGN PATENT DOCUMENTS

| | | | |
|---|---|---|---|
| 0076493 | 4/1983 | European Pat. Off. | 512/6 |
| 75279 | 9/1980 | Romania | 512/8 |

OTHER PUBLICATIONS

Miyano, et al, title "C-Alkylation of Active Methylene Compounds by means of Alcohols. VI. A Facile Monoalkylation of Phenylacetonitrile", J. Org. Chem., vol. 36, No. 20, 1971, pp. 2948-2951.

Xu, et al, title "Alkylation Of Phenylacetonitrile Using Potassium Carbonate As A Base", Organic Preprea- tions And Procedure Int. 23(2), 153-156, (1991).

Overberger, et al, title "Ionic Polymerization. A Convenient Synthesis of alpha– and beta-Alkyl-styrenes. The Effect Of An alpha-Alkyl Group On The Ultraviolet Absorption Spectra", Journal of The American Chemical Society, Jan. 20, 1955, vol. 77, pp. 369-373.

Goerner, et al, title "Selected Phenyl-2-methyl-hex- anes", J. Org. Chem., Oct. 1959, vol. 24, pp. 1561-1563.

FMA TM Trademark And Coined Names Catalogue, Fragrance Materials Association Of The United States, Inc., Washington, D.C., Title page, Code of Company Abbreviations, Replacement Page Jul. 31, 1984; pp. T1 and p. co10.

Chemical Abstracts, vol. 114:101251k (abstract of Saku- rai, et al Yakugaku Zasshi, 1990, 110(10), 737-745.

Primary Examiner—James H. Reamer
Attorney, Agent, or Firm—Arthur L. Liberman

[57] ABSTRACT

Described are 1-phenyl-1-cyano-$C_5$-$C_7$ alkanes defined according to the structure:

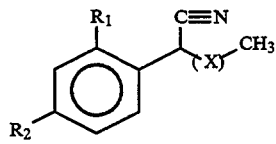

wherein $R_1$ and $R_2$ each represents hydrogen or methoxy with the proviso that when $R_1$ is methoxy, $R_2$ is hydrogen and when $R_2$ is methoxy, $R_1$ is hydrogen; and wherein X is $C_3$-$C_5$ straight chain or branched chain alkylene and uses thereof in augmenting, enhancing or modifying perfume compositions, perfumed articles and colognes. Also described is a process for preparing such 1-phenyl-1-cyano-$C_5$-$C_7$ alkanes by means of reacting benzyl cyanide with an aldehyde or ketone and then hydrogenating the resulting product using a supported palladium catalyst.

9 Claims, 32 Drawing Sheets

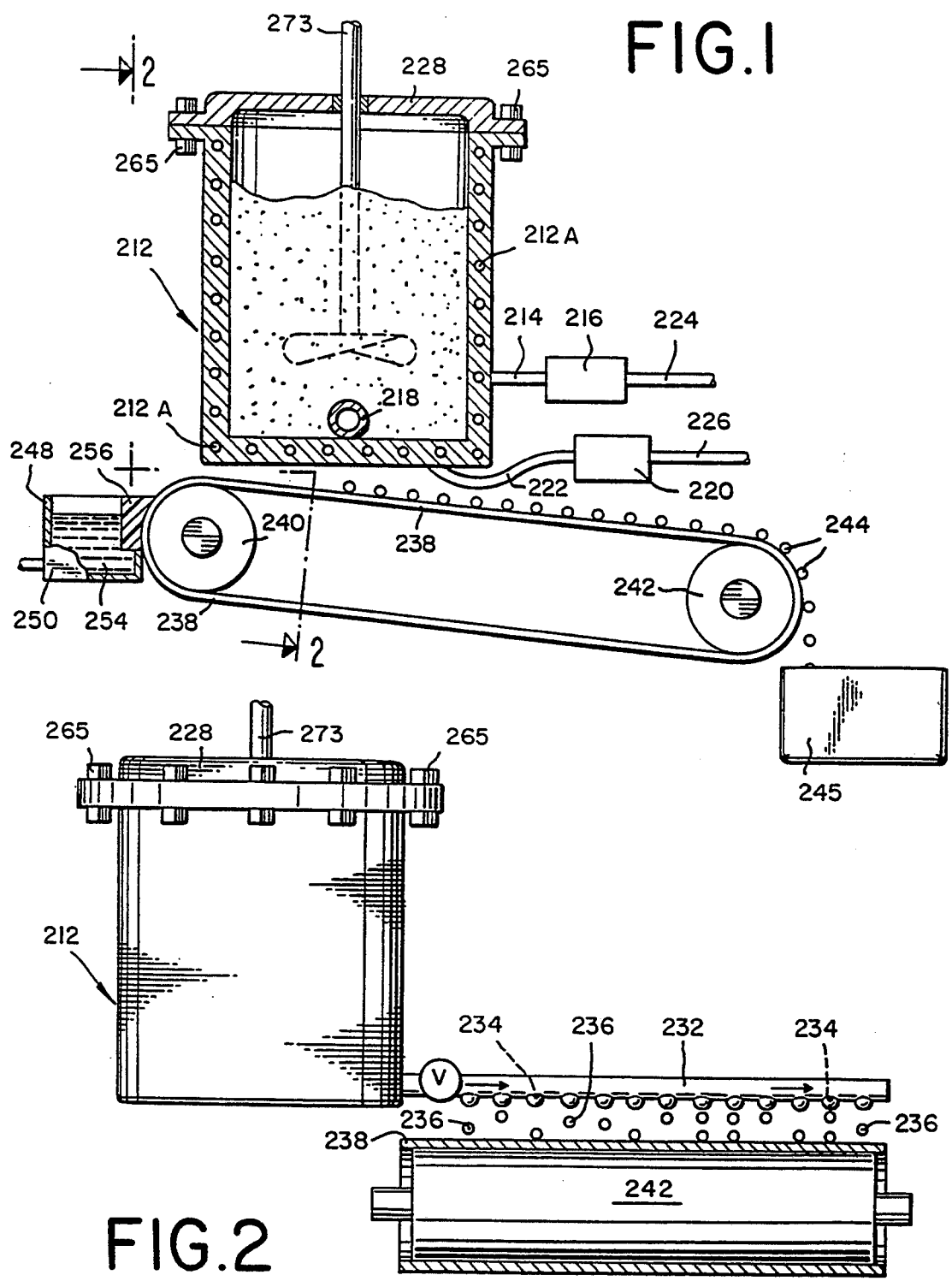

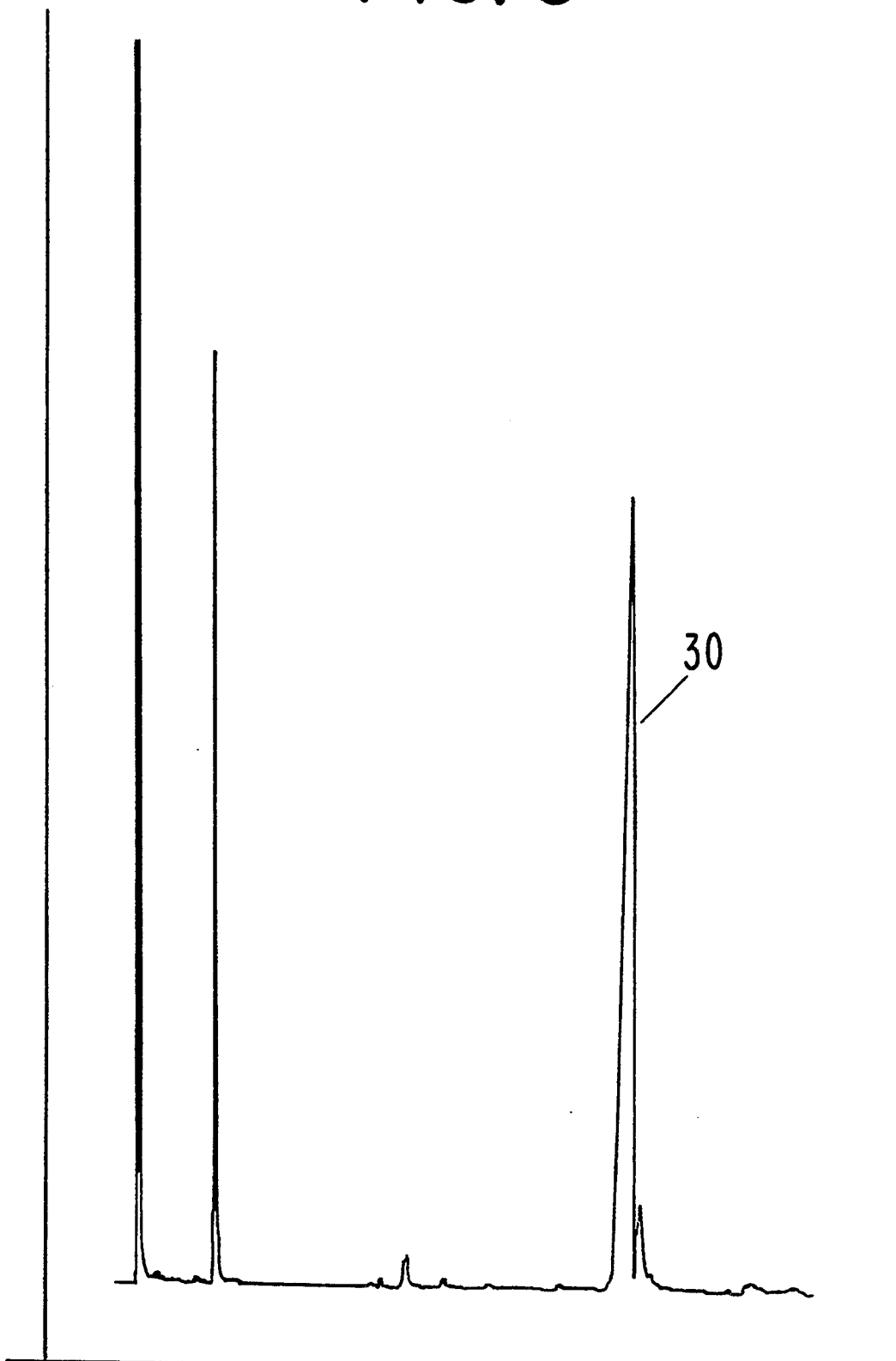

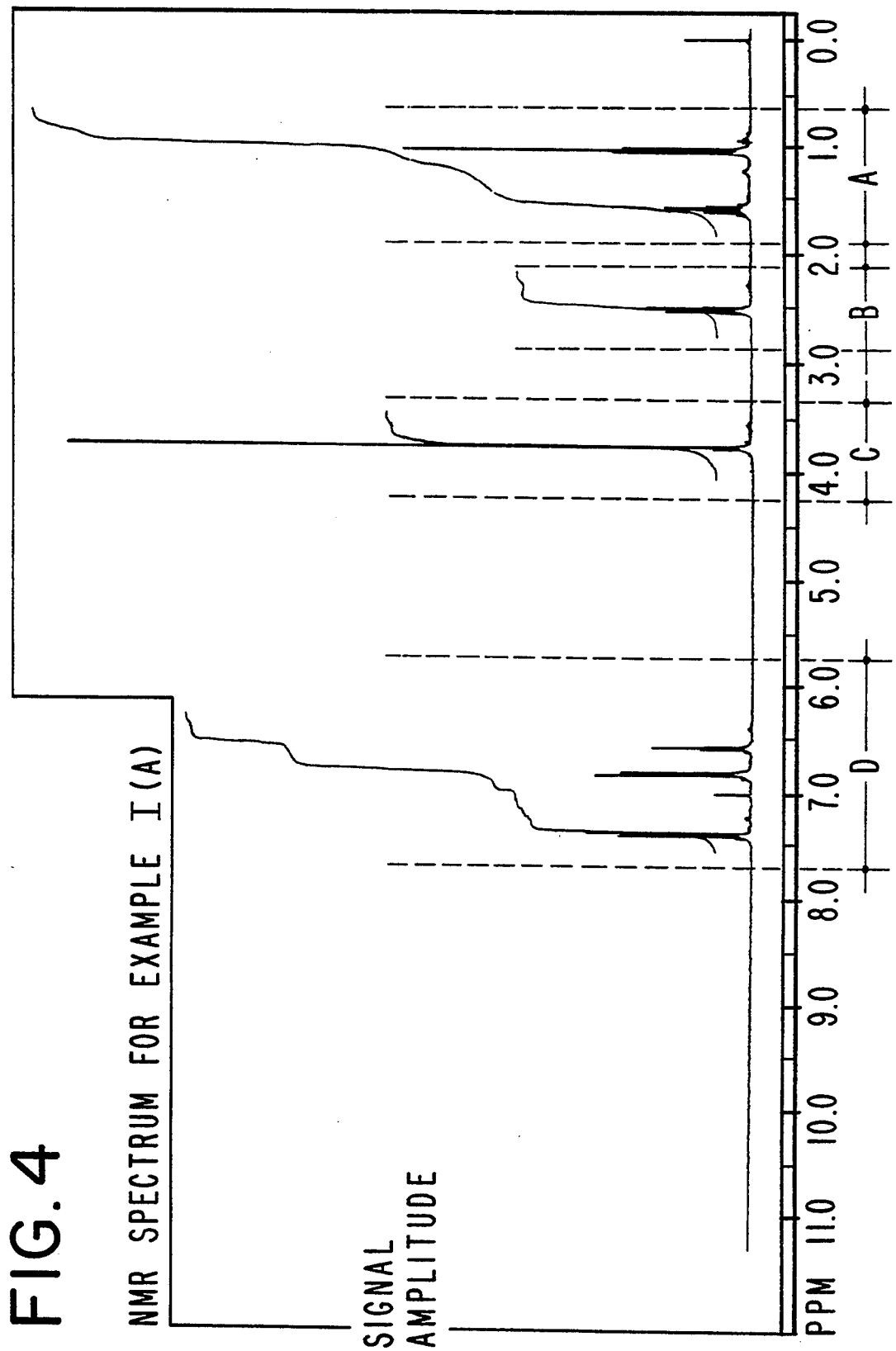

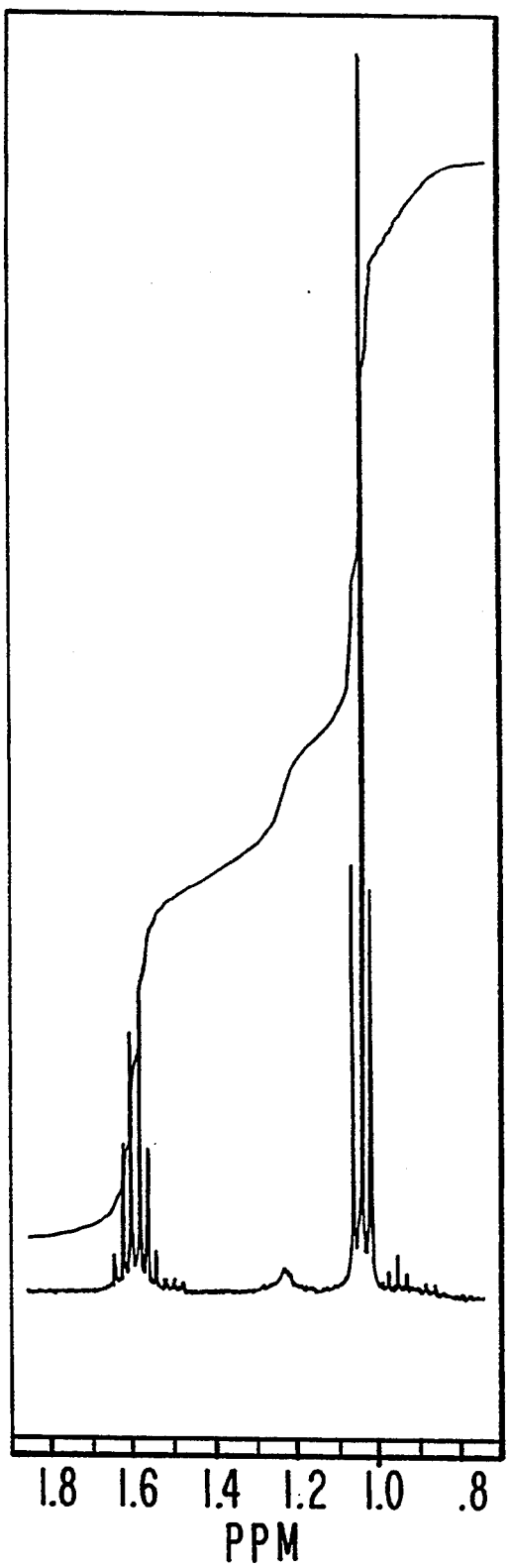
FIG. 4-A
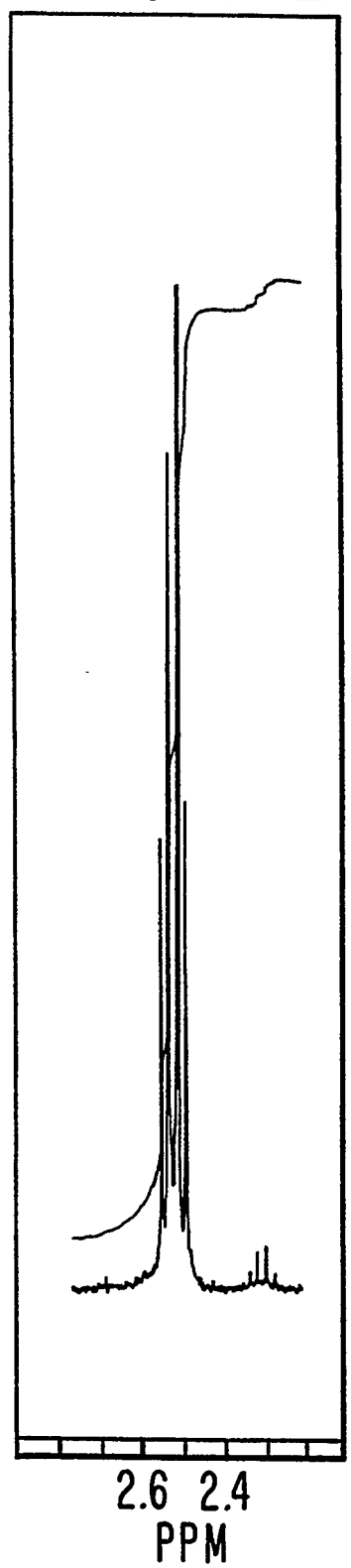
FIG. 4-B

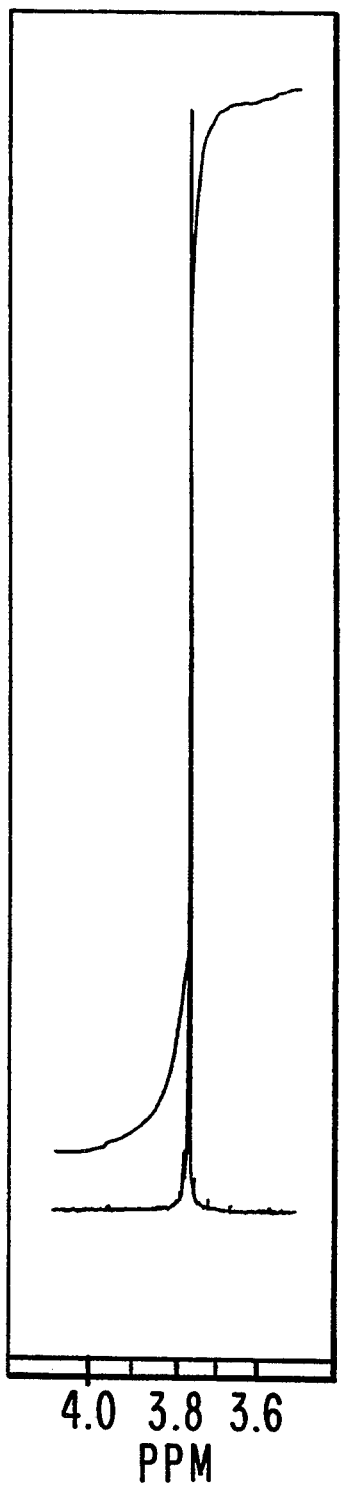
FIG. 4-C
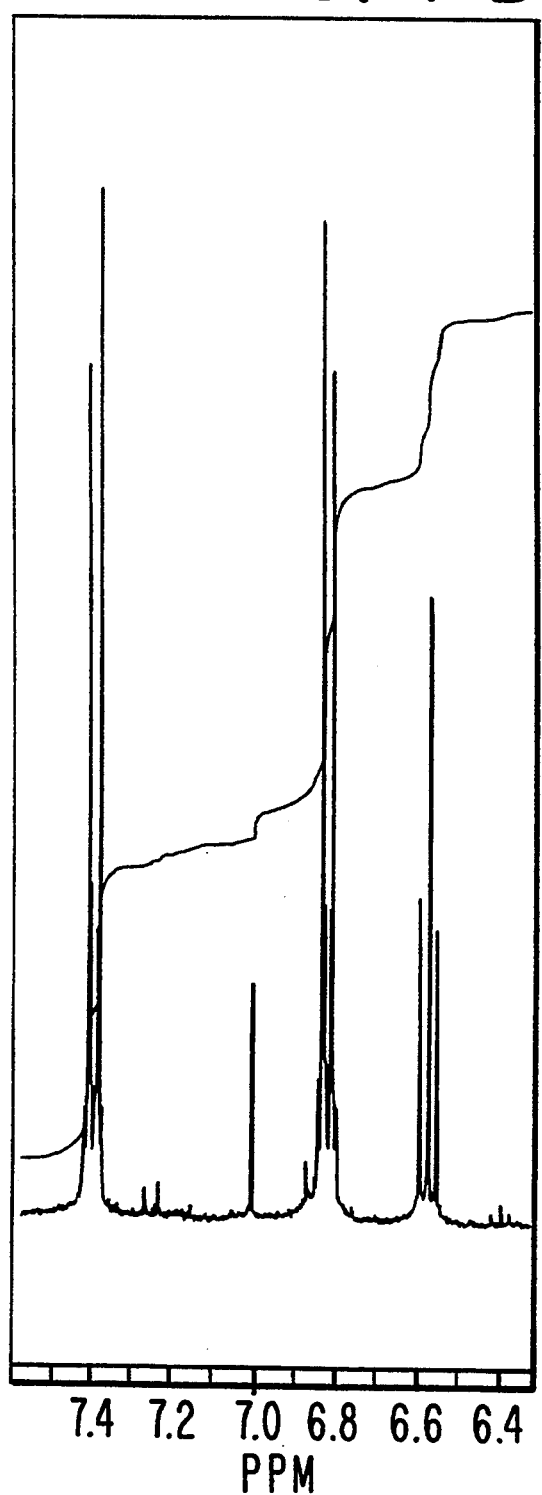
FIG. 4-D

GLC PROFILE FOR EXAMPLE I(B)

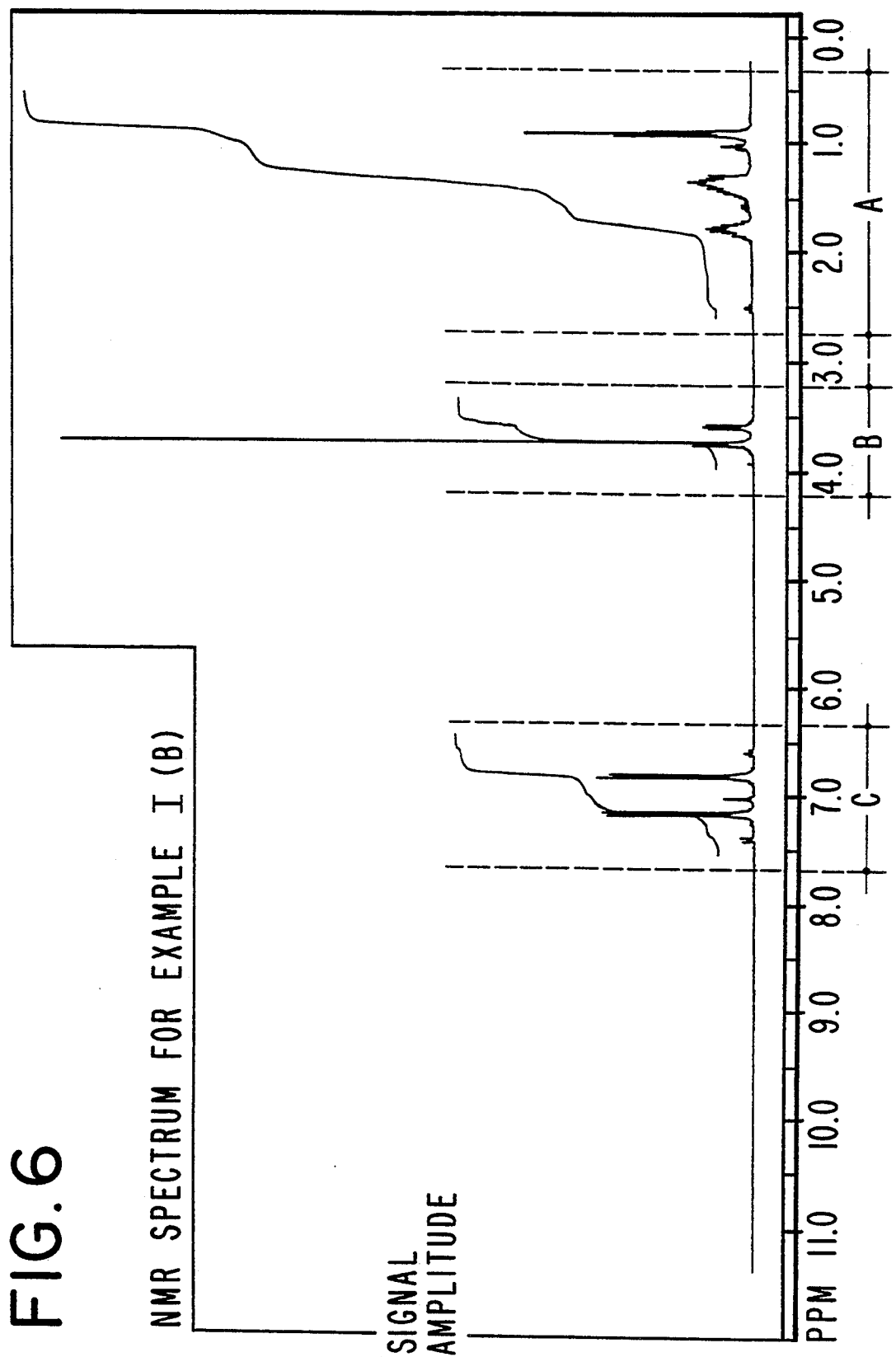

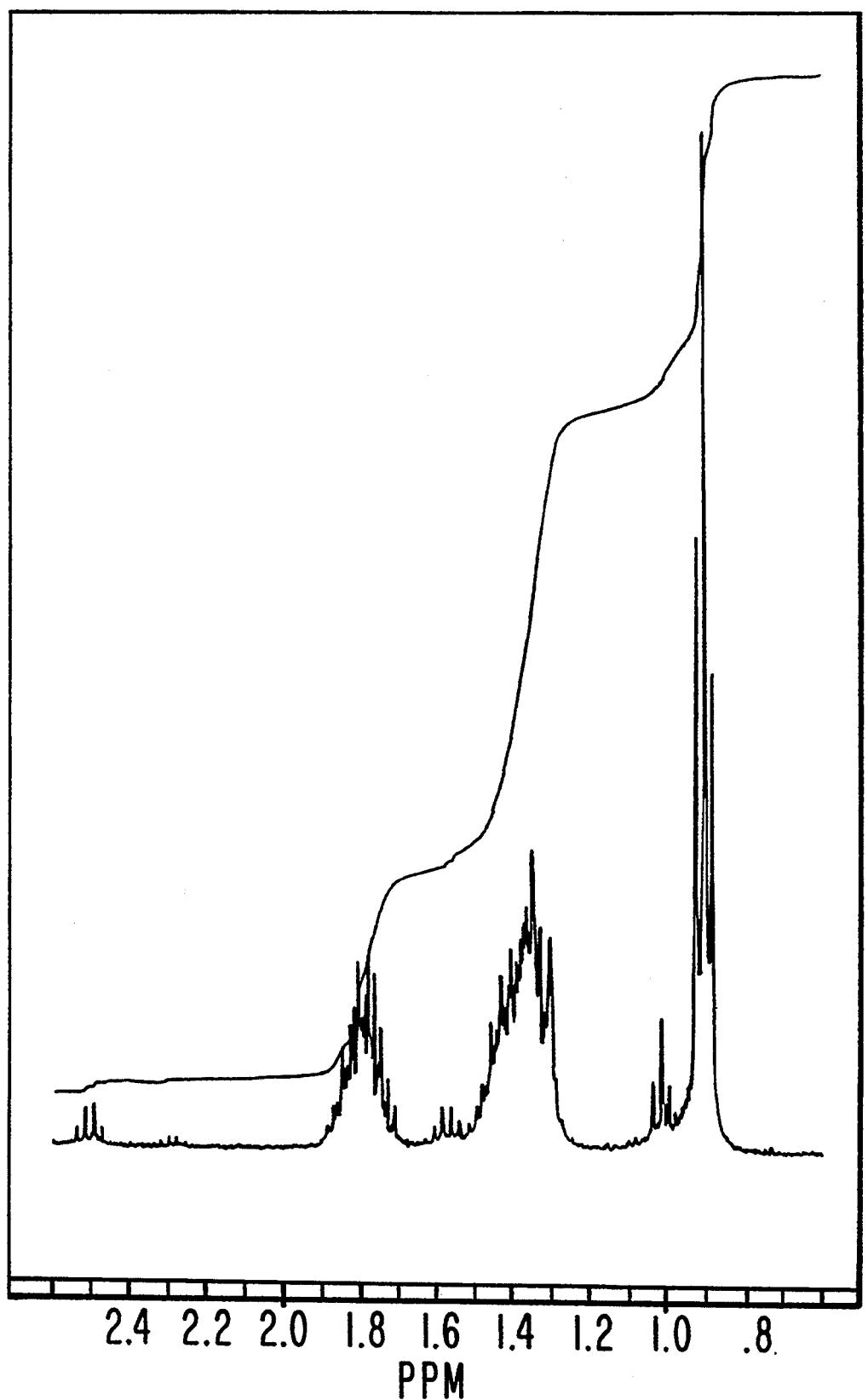
FIG. 6-A

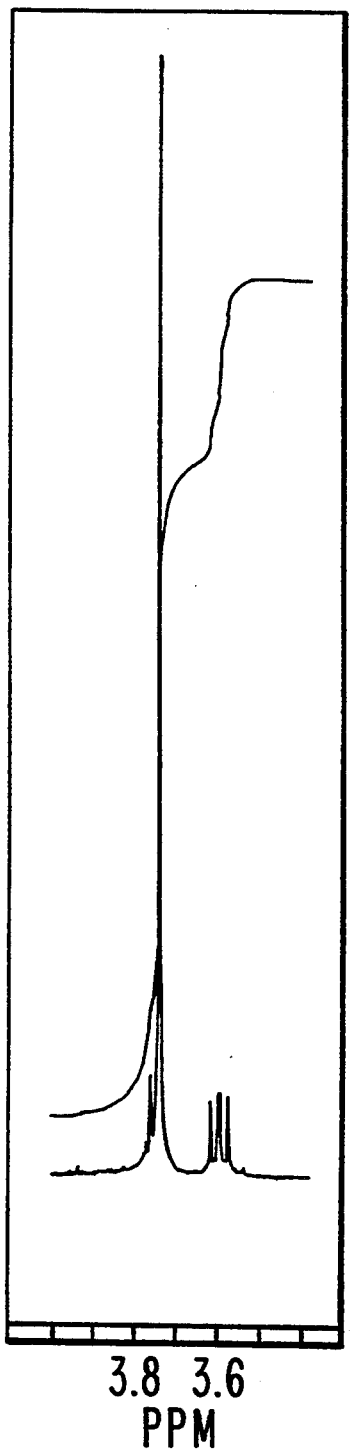
FIG. 6-B
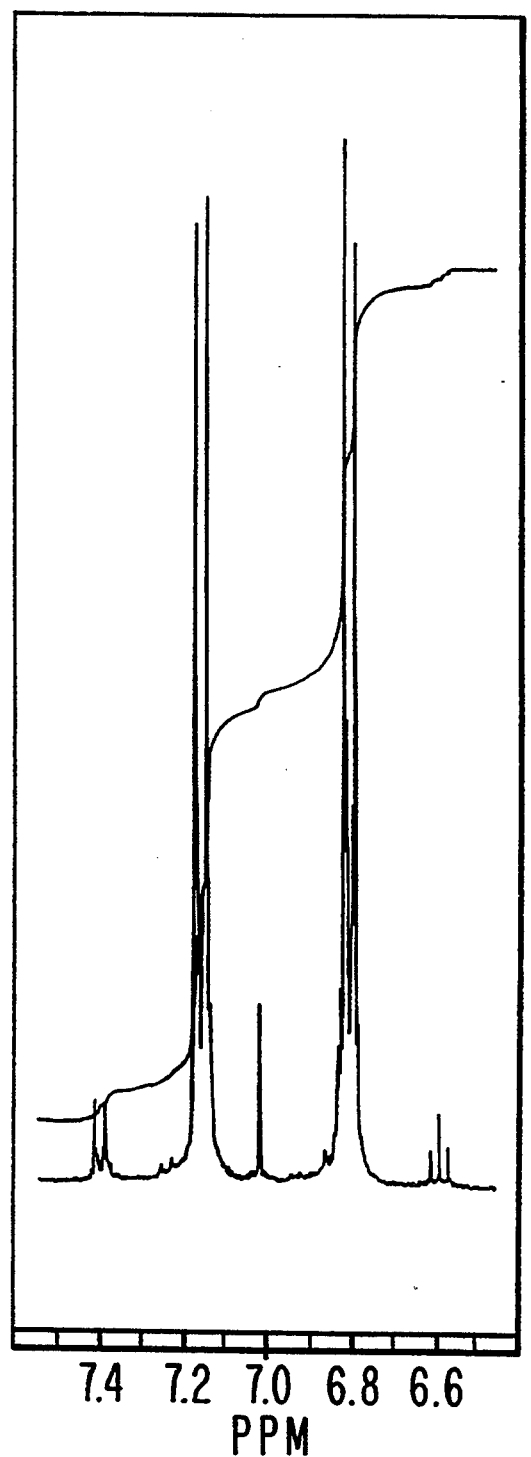
FIG. 6-C

GLC PROFILE FOR EXAMPLE II (A)

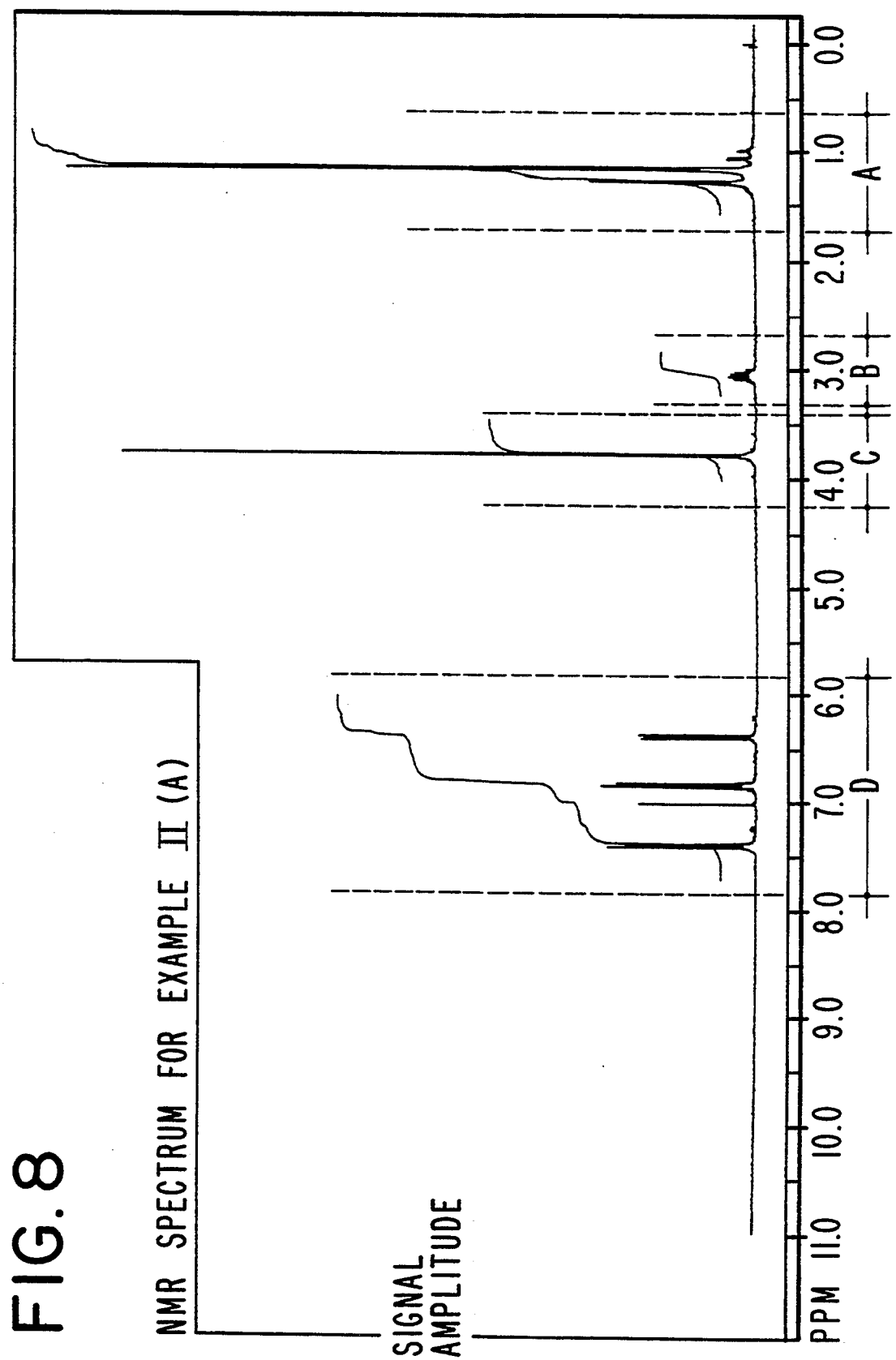
FIG. 8 NMR SPECTRUM FOR EXAMPLE II (A)

FIG. 8-A
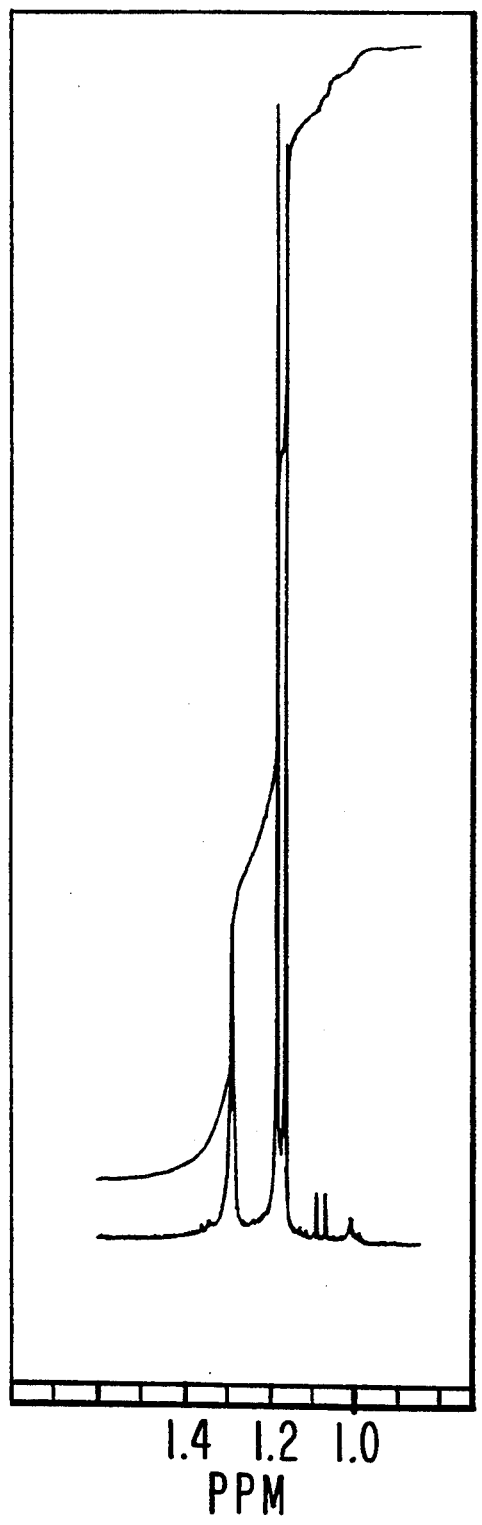
FIG. 8-B
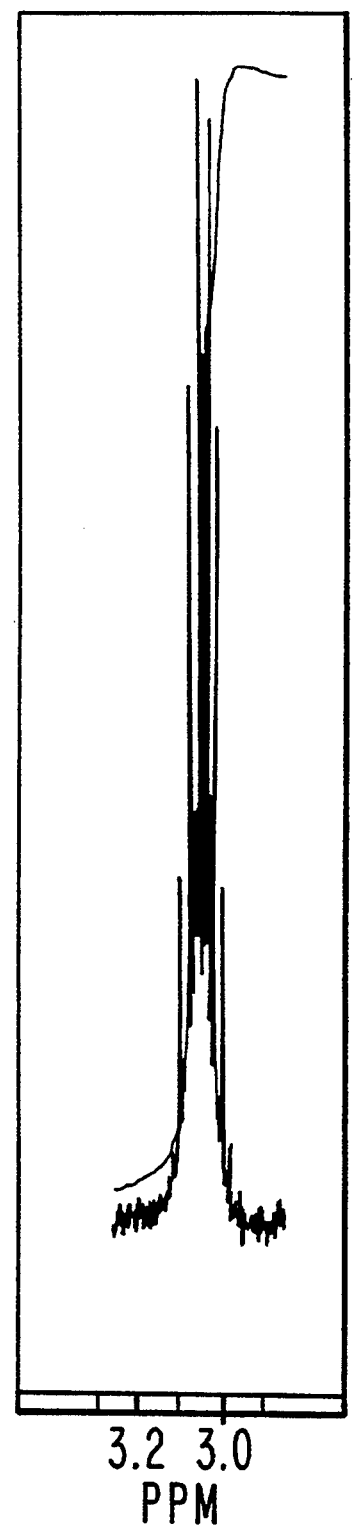

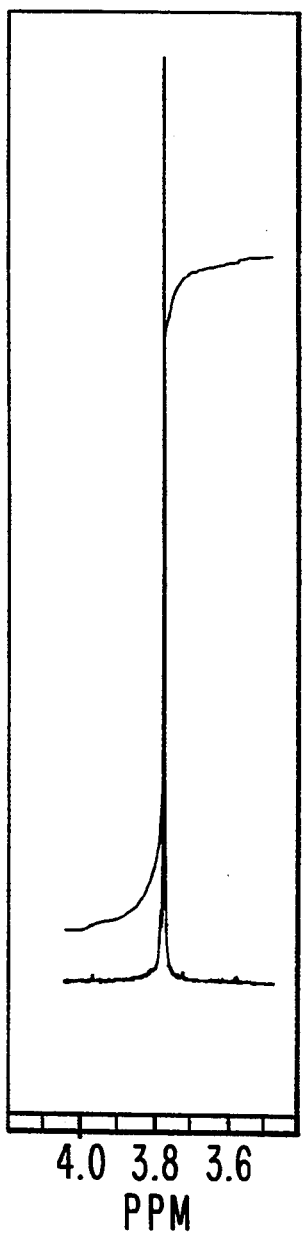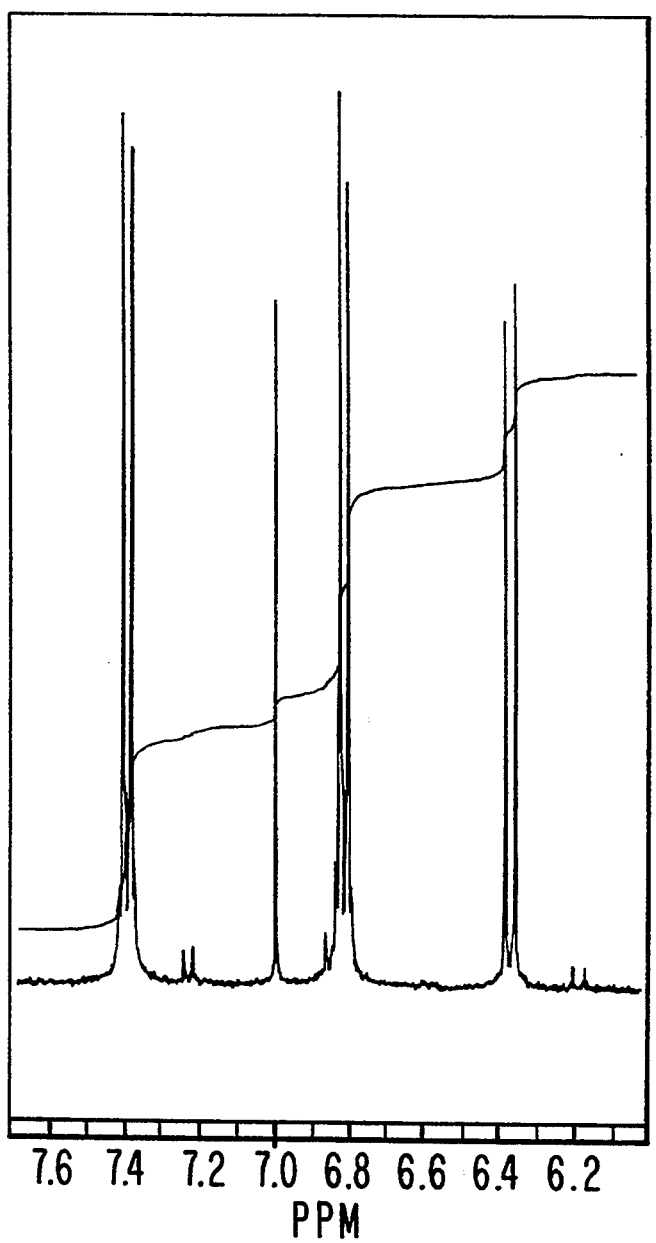

GLC PROFILE FOR EXAMPLE II (B)

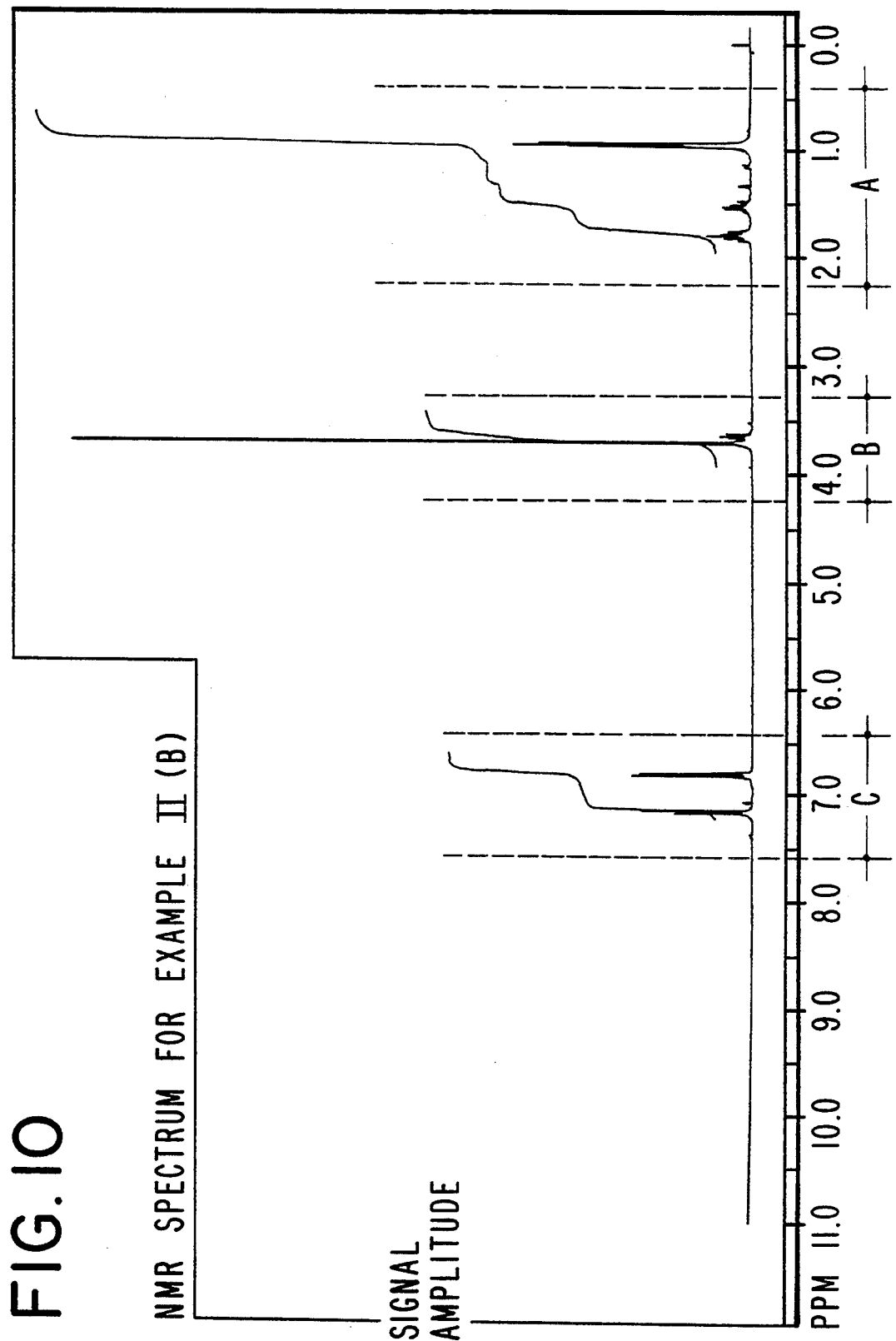
FIG. 10 NMR SPECTRUM FOR EXAMPLE II (B)

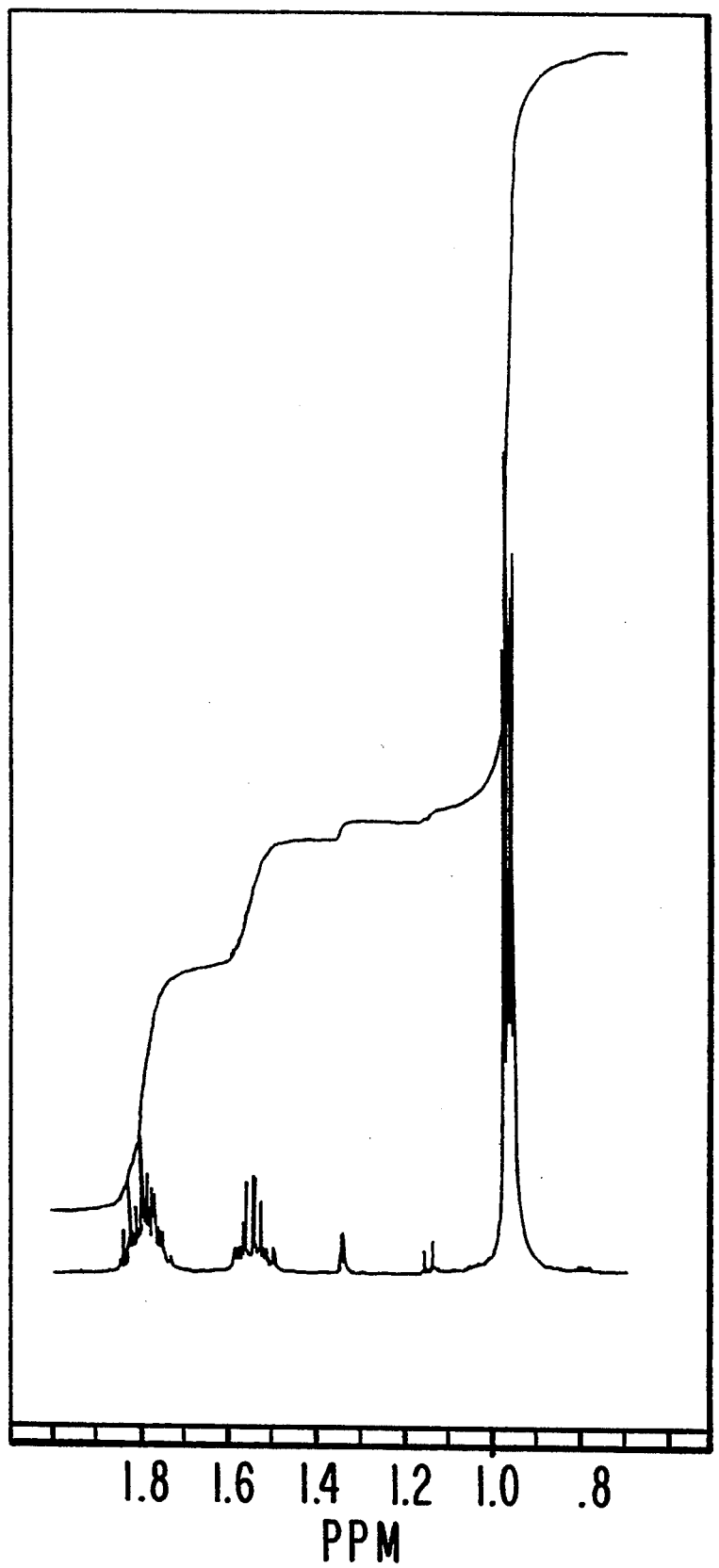

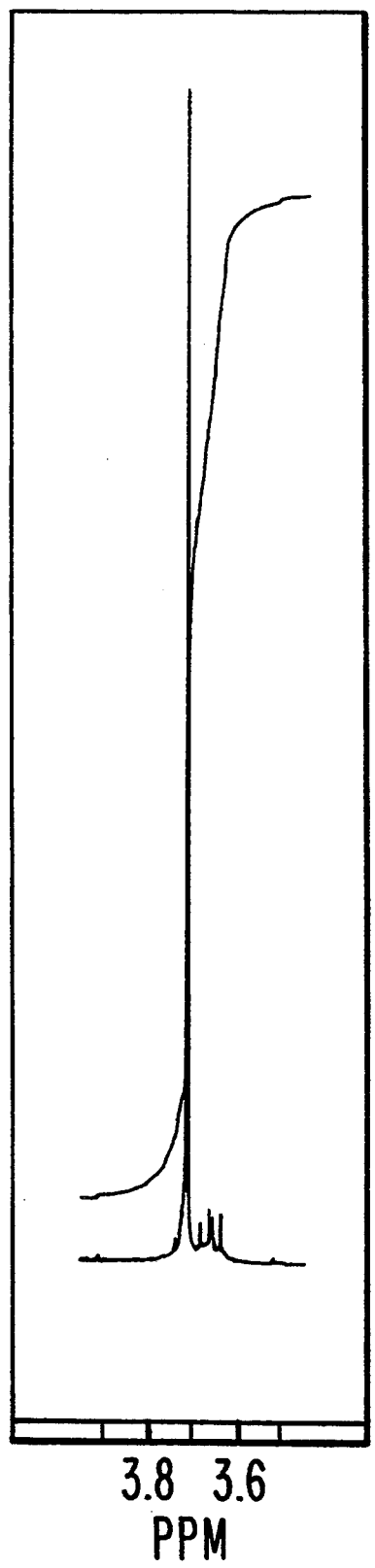
FIG.10-B
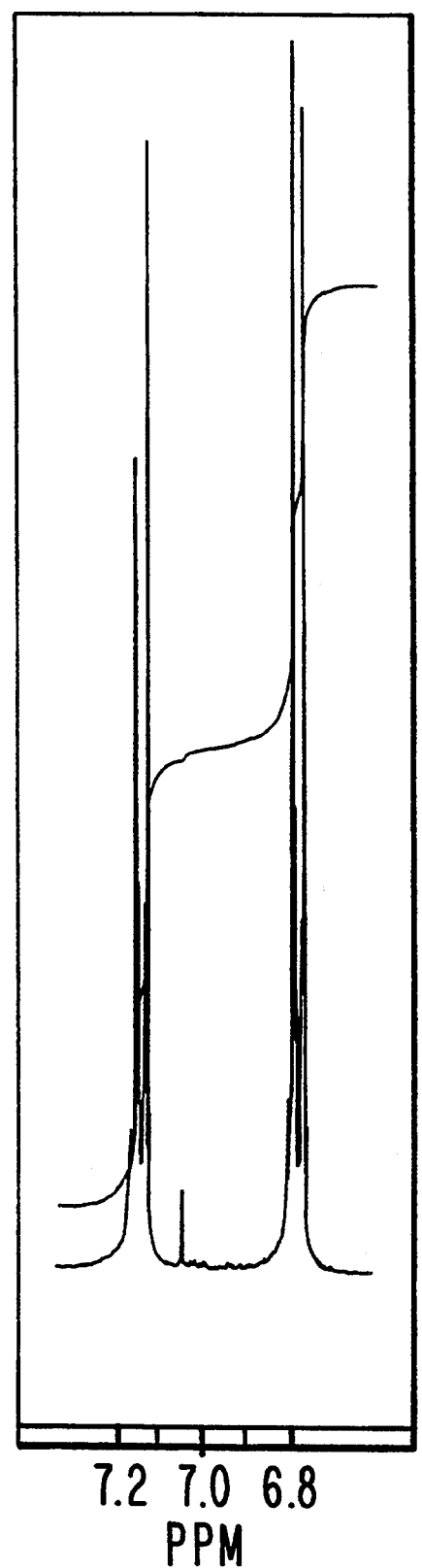
FIG.10-C

GLC PROFILE FOR EXAMPLE III (A)

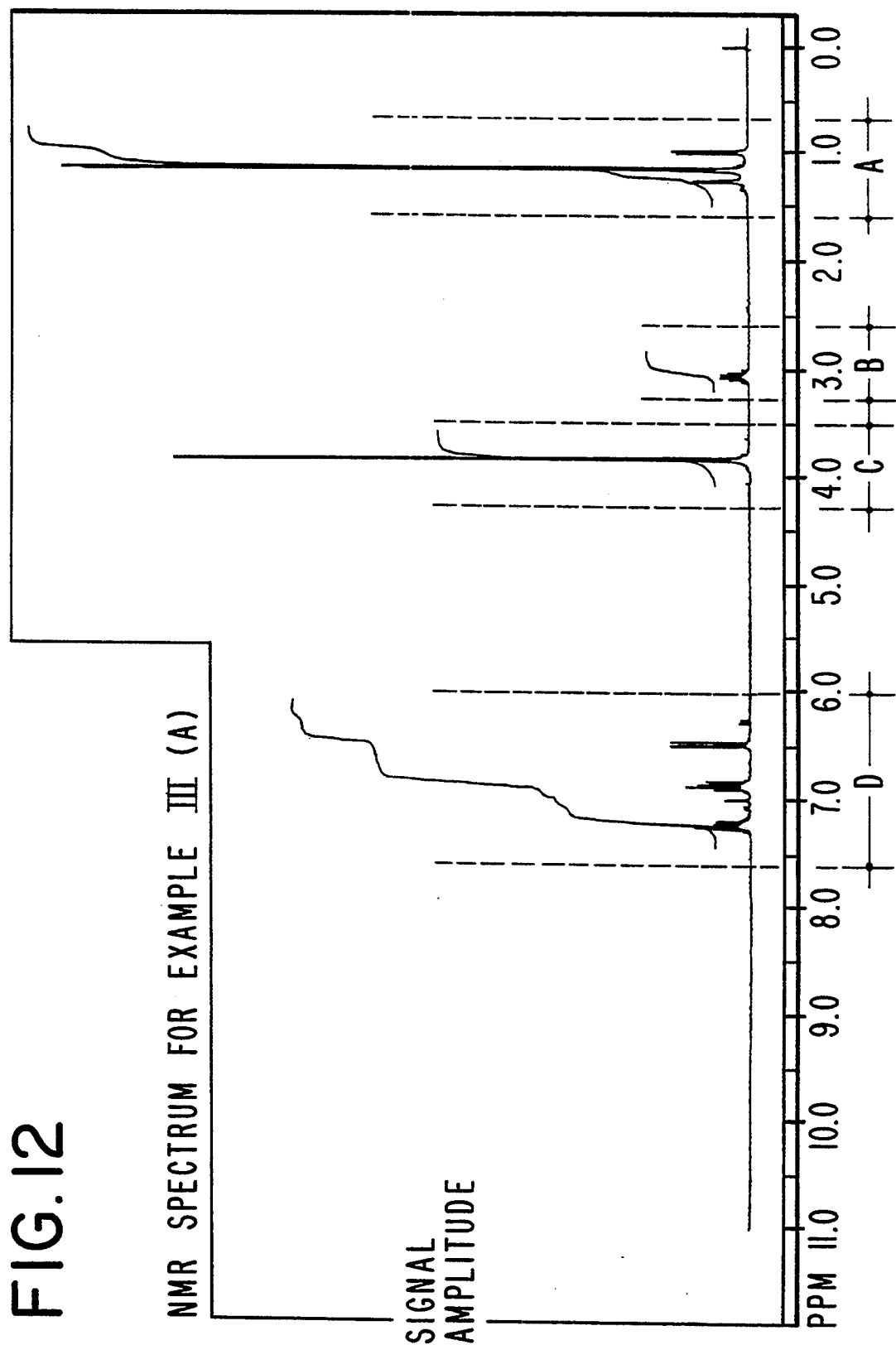
FIG. 12 NMR SPECTRUM FOR EXAMPLE III (A)

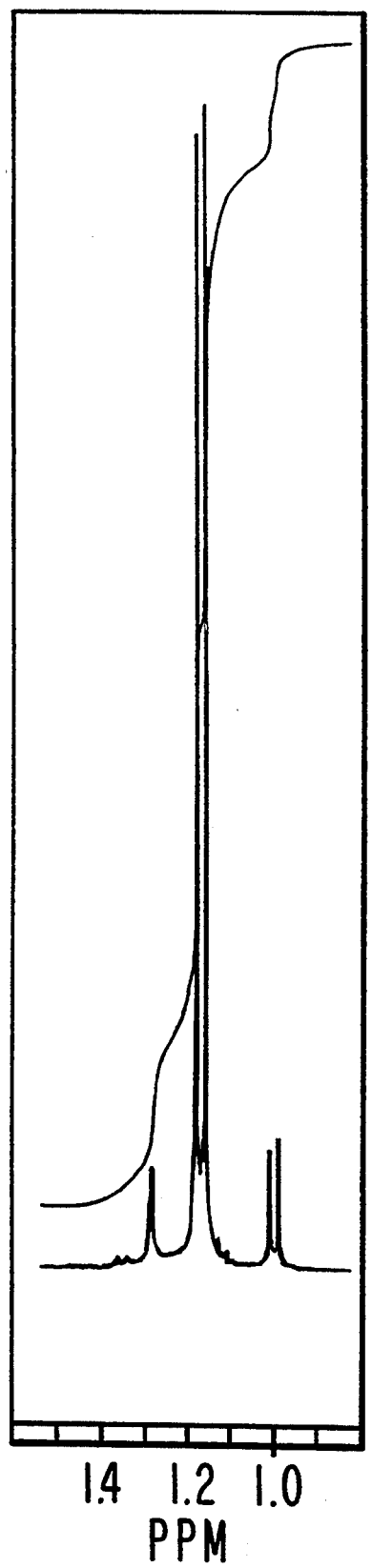
FIG. 12-A
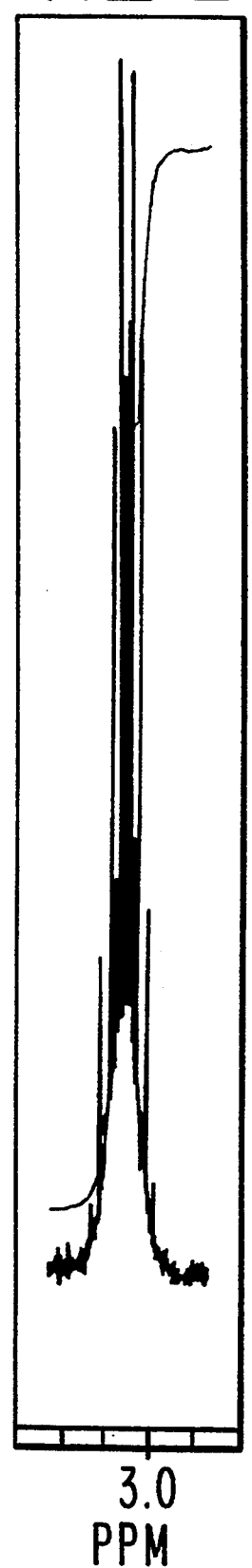
FIG. 12-B

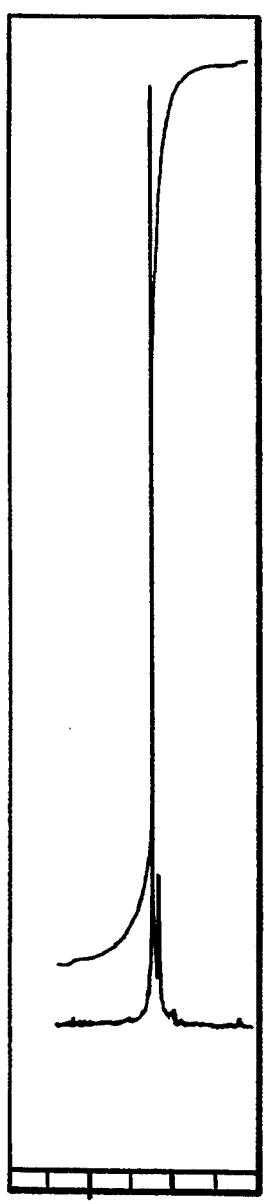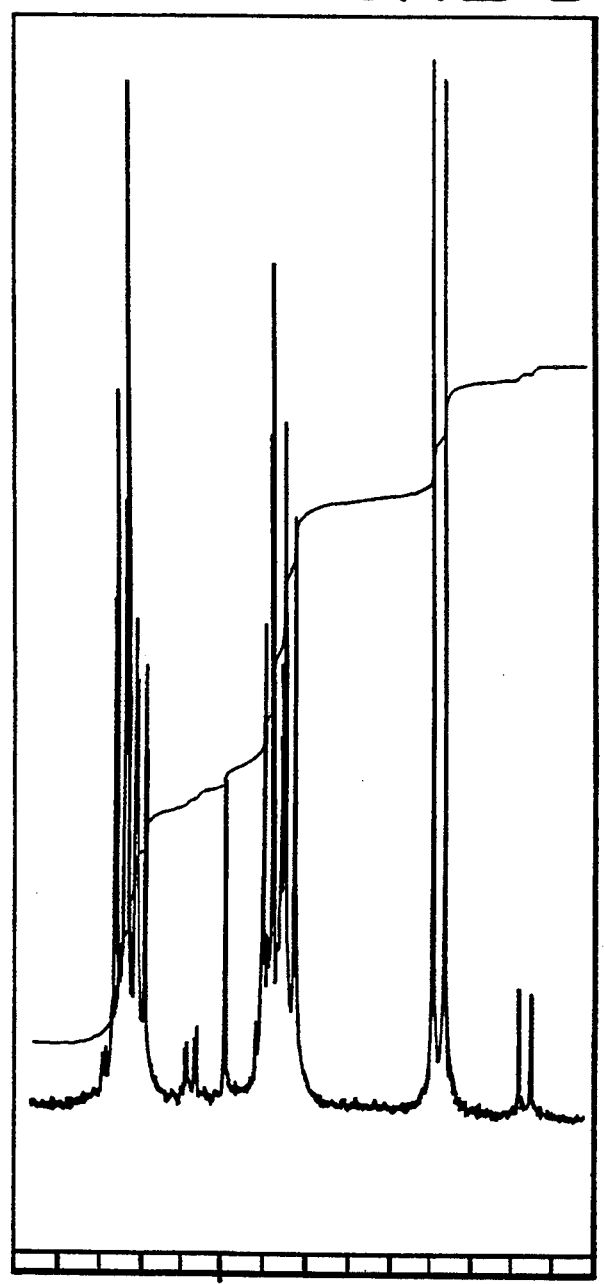

GLC PROFILE FOR EXAMPLE III (B)

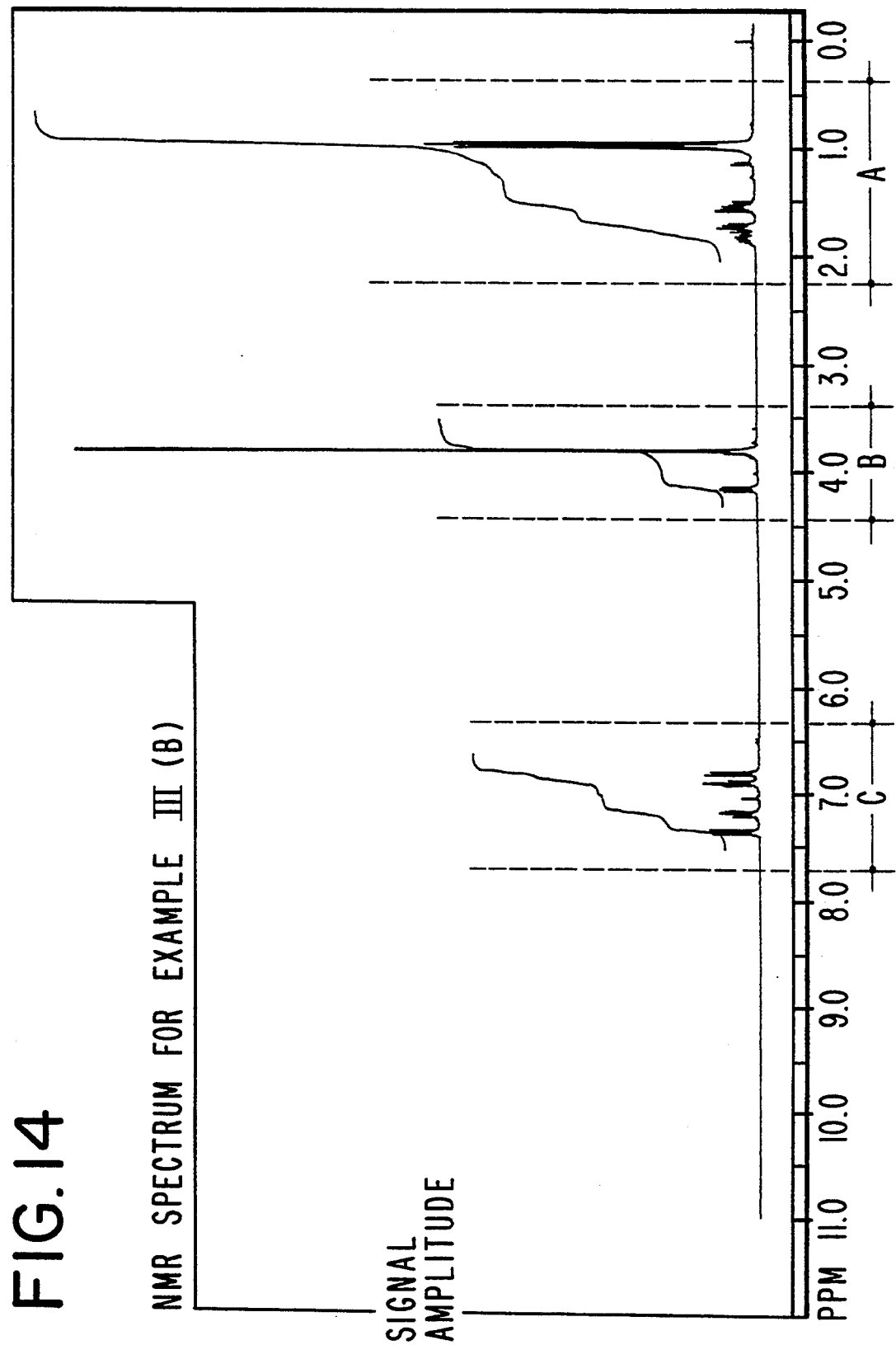

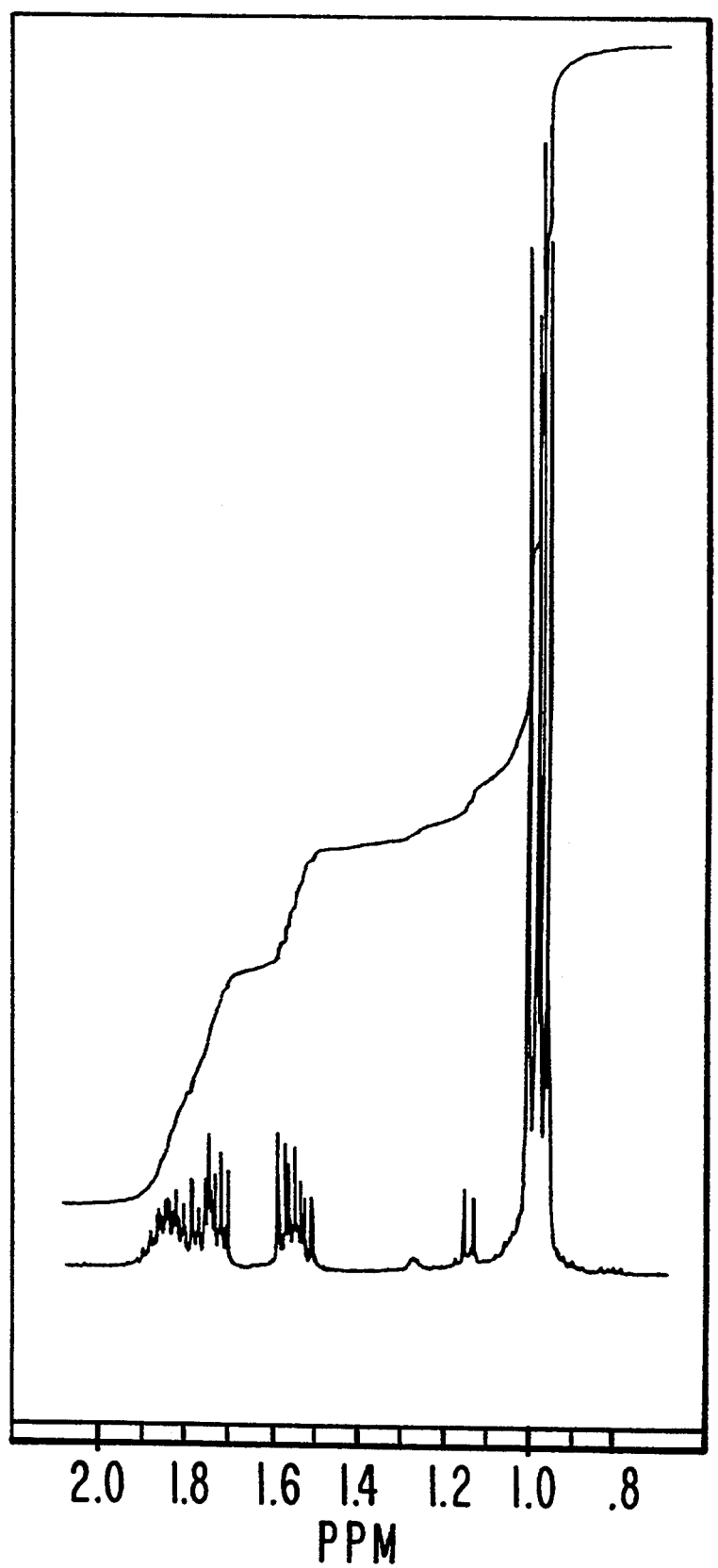
FIG. 14-A

FIG.14-B
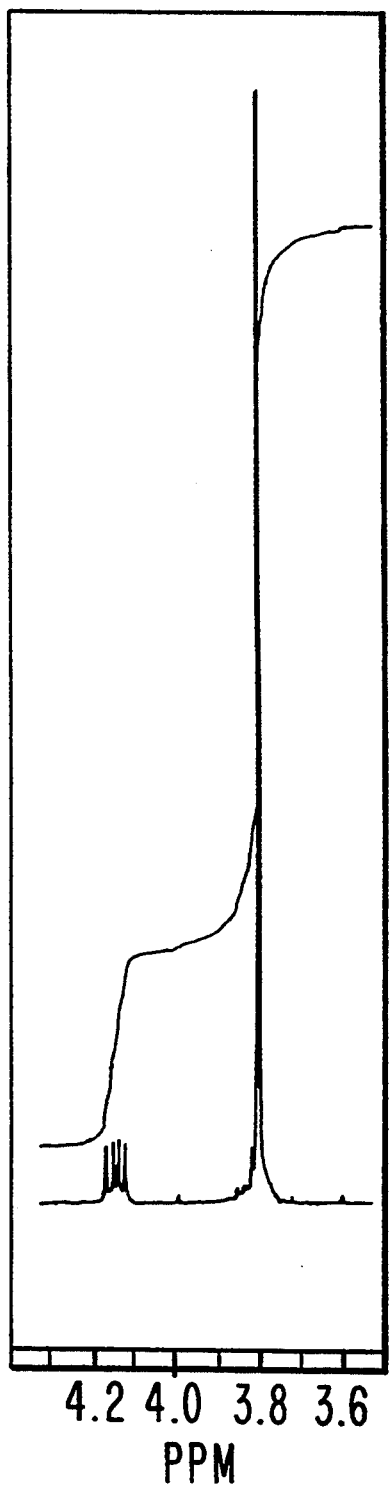
FIG.14-C
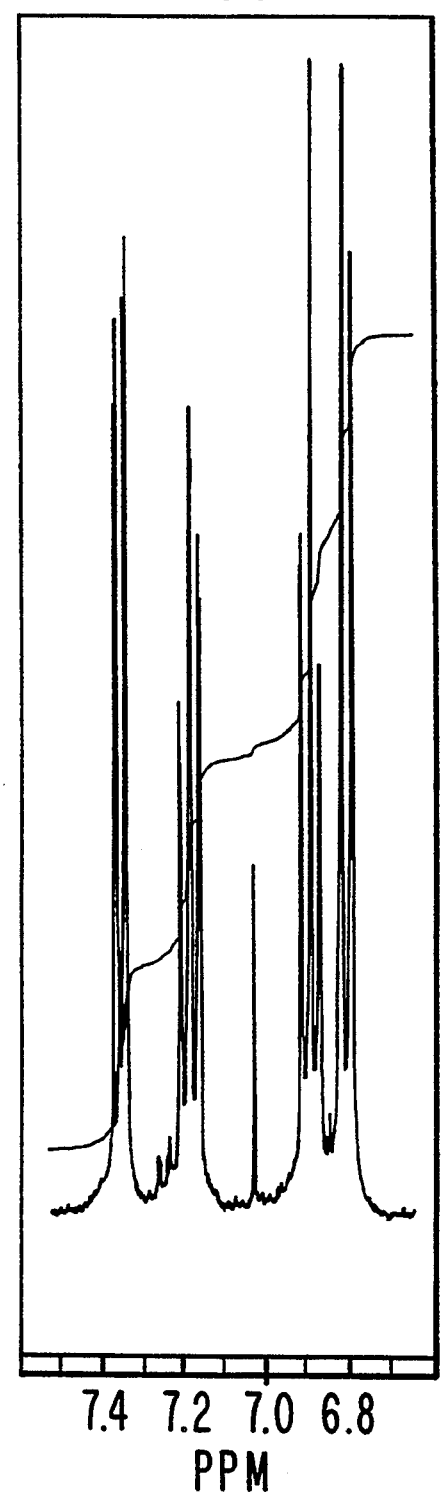

GLC PROFILE FOR EXAMPLE IV (A)

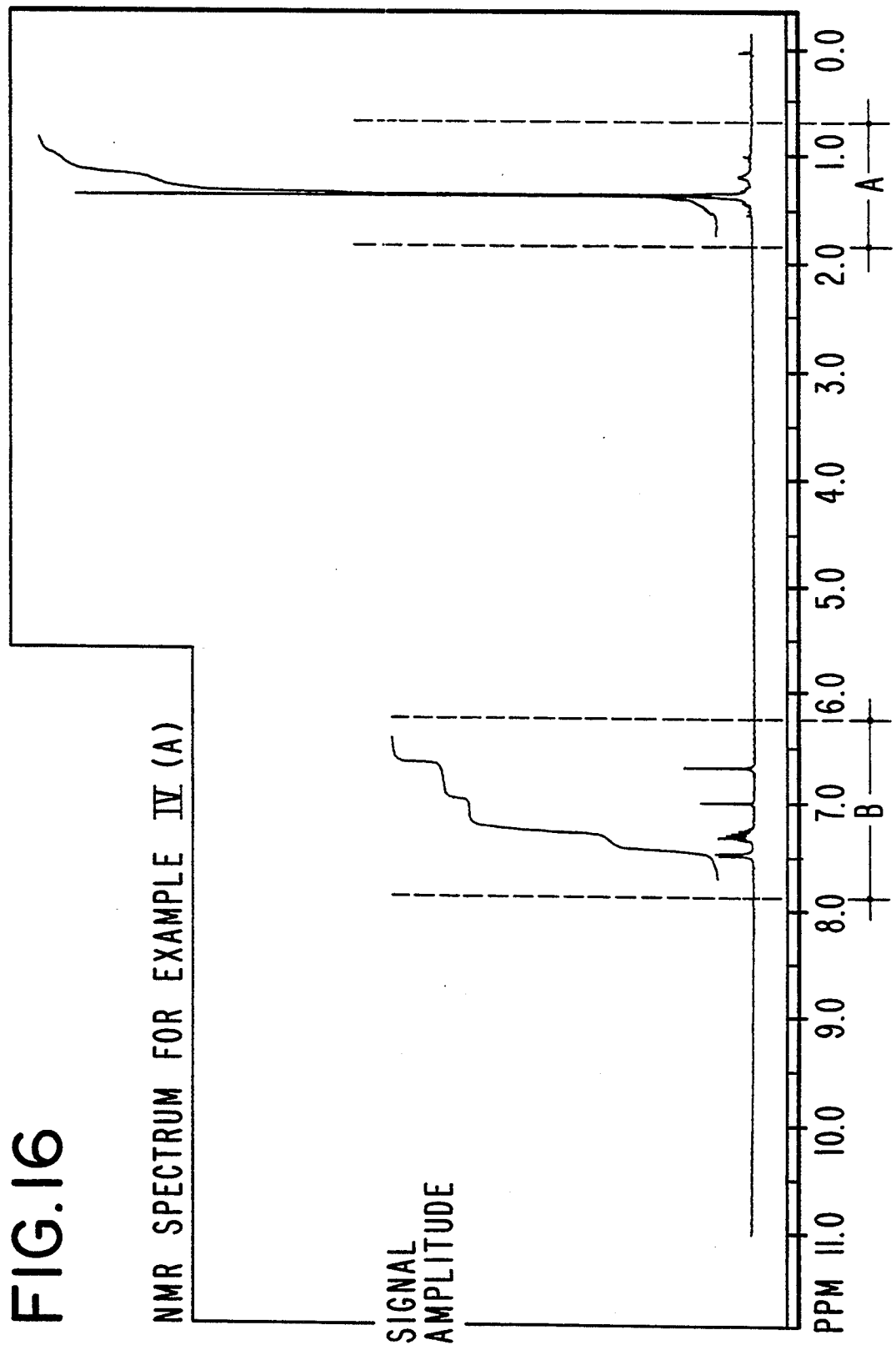
FIG. 16 NMR SPECTRUM FOR EXAMPLE IV (A)

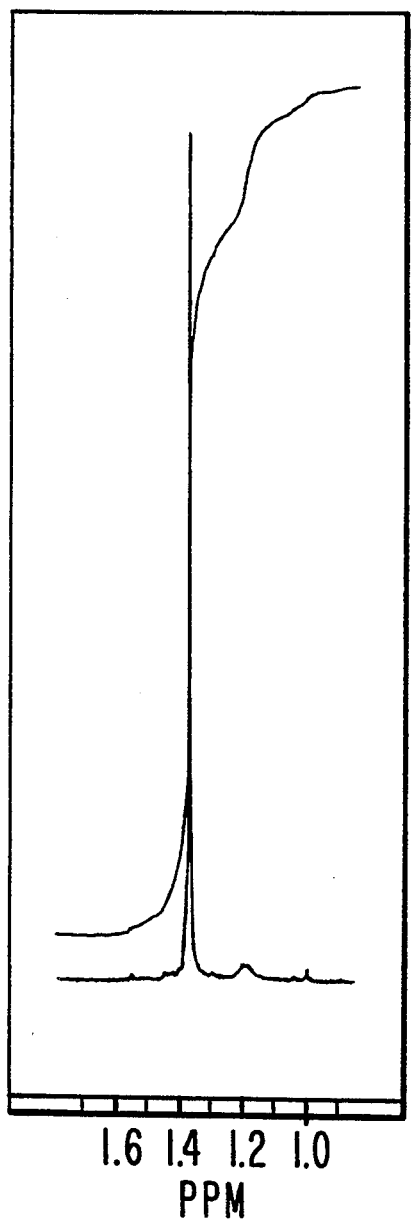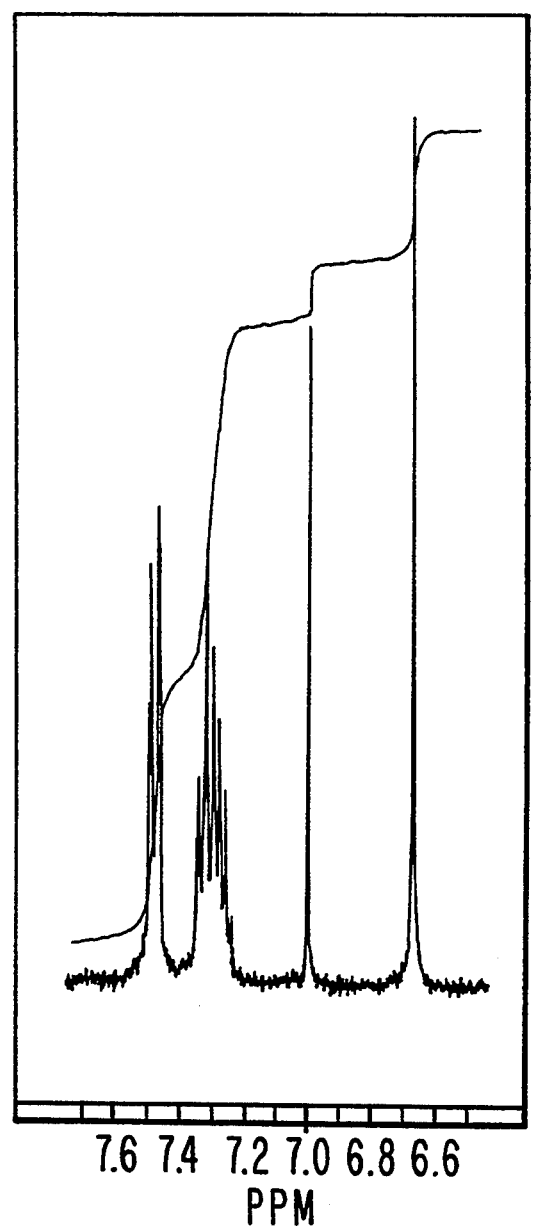
FIG. 16-A
FIG. 16-B

GLC PROFILE FOR EXAMPLE IV(B)

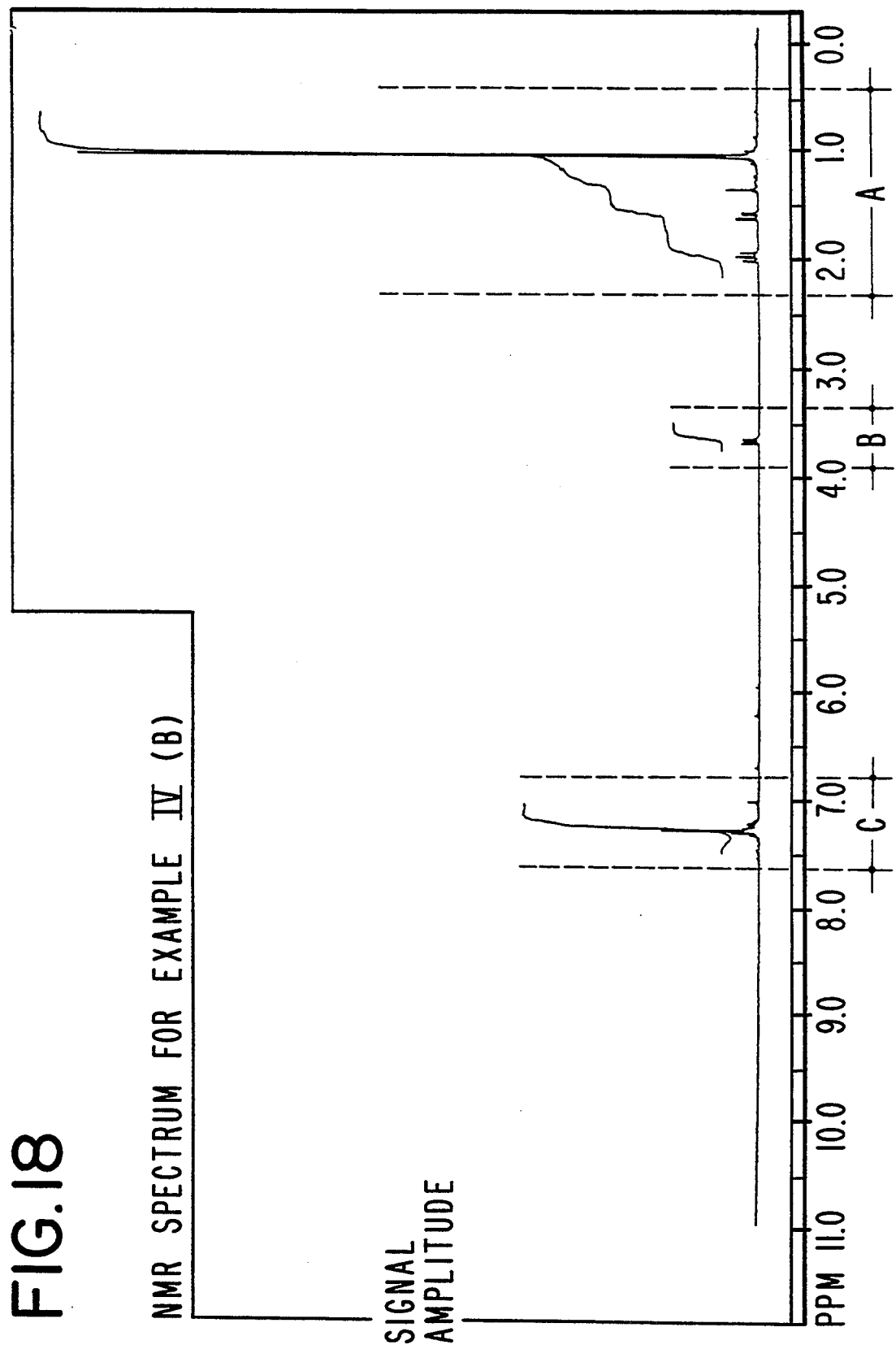
FIG. 18 NMR SPECTRUM FOR EXAMPLE IV (B)

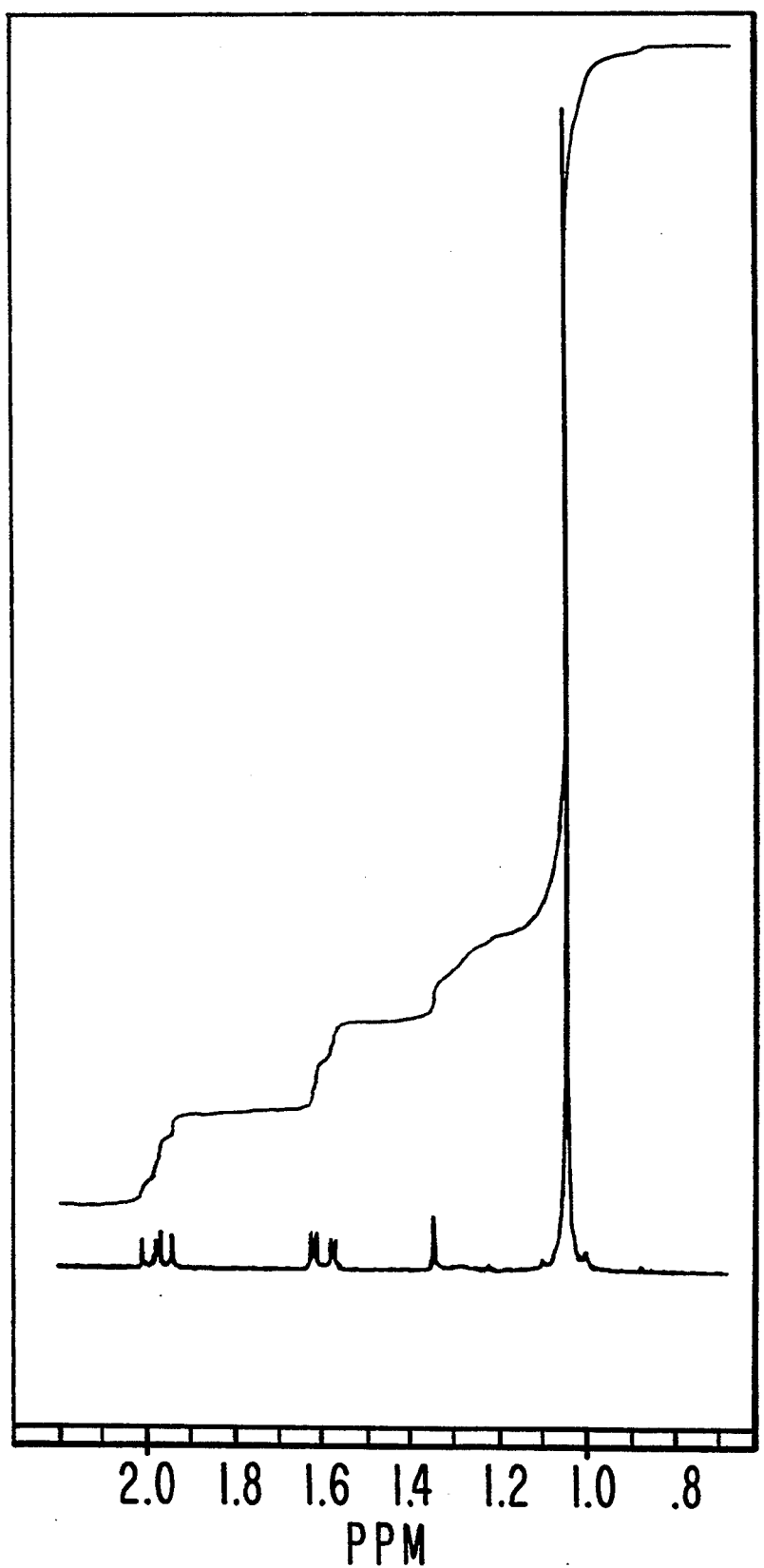
FIG. 18-A

FIG.18-B
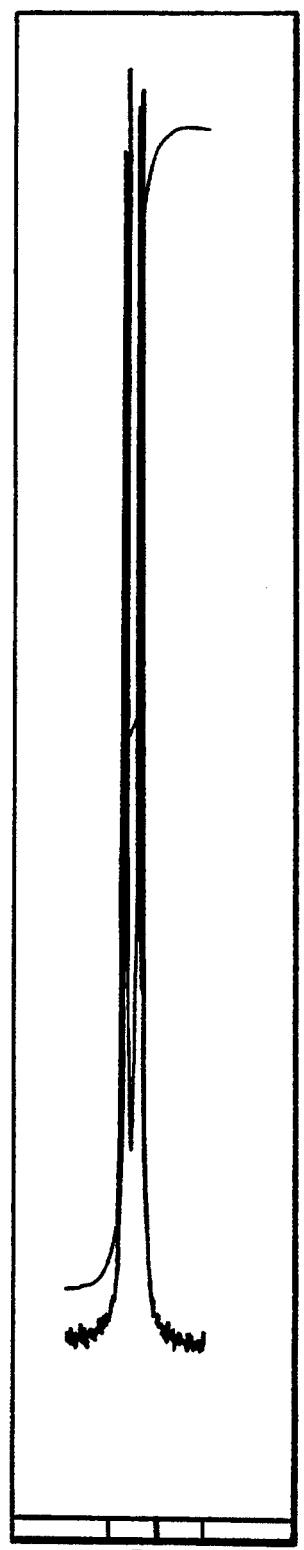
3.6
PPM
FIG.18-C
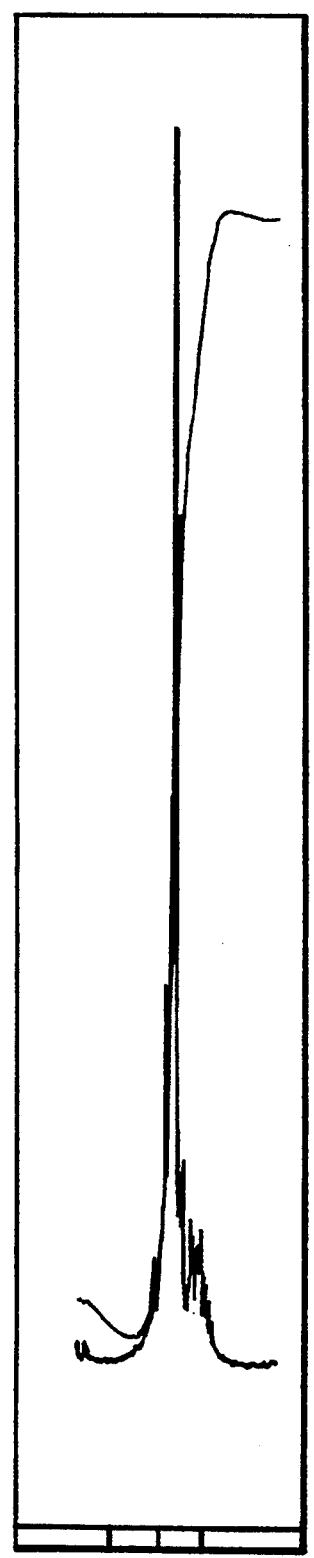
7.4  7.2
PPM

1-PHENYL-1-CYANO-C$_5$-C$_7$ ALKANES, ORGANOLEPTIC USES THEREOF AND PROCESS FOR PREPARING SAME

BACKGROUND OF THE INVENTION

Our invention relates to 1-phenyl-1-cyano-C$_5$-C$_7$ alkanes defined according to the structure:

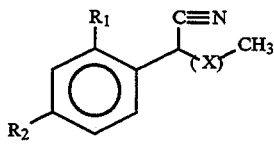

wherein R$_1$ and R$_2$ each represents hydrogen or methoxy with the proviso that when R$_1$ is methoxy, R$_2$ is hydrogen and when R$_2$ is methoxy, R$_1$ is hydrogen; and wherein X represents C$_3$-C$_5$ straight chain or branched chain alkylene. Our invention also covers the specific compounds having the structures:

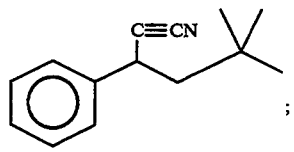

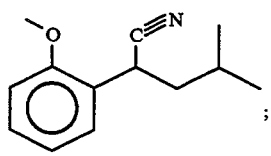

and

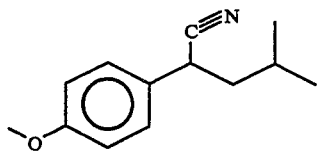

as novel compounds. Our invention also covers the uses of the compounds defined according to the generic structure:

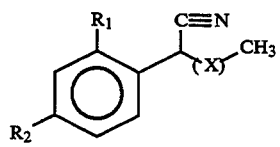

for their organoleptic (e.g., perfumery) properties. Our invention also covers processes for preparing the compounds defined according to the generic structure:

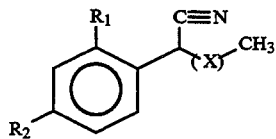

by means of reacting benzyl cyanide with an aldehyde or ketone and then hydrogenating the resulting product using a supported palladium catalyst.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Long-lasting, intense, and substantive floral, rose, muguet, herbal, green, fruity, pineapple-like, salicylate, basil, sweet, living orange flower, almond, cherry, woody, cigar box-like, ambergris, animalic, honey-like, musky, balsamic, cedarwood and sage-like aromas, with sweet, woody, fruity, wine-like, green, salicylate, animalic, honey-like, floral, rose, cabreuva oil-like and bois-de-rose topnotes, and sweet, green, floral, muguet, rose, salicylate, anethole-like, carvone-like, costus and almondy undertones and with a "cooling" effect on the skin on dry-out are highly desirable in several types of perfume compositions, perfumed articles and colognes (e.g., floral fragrances).

The perfume uses of nitrile-containing derivatives which contain phenyl moieties are well known in the prior art. Thus, the compounds defined according to the structure:

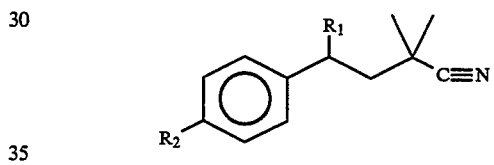

wherein R$_1$ and R$_2$ are the same or different and each represents hydrogen or methyl are disclosed in U.S. Pat. No. 5,143,899 issued on Sep. 1, 1992 (title "Process For Preparing Phenyl Butyronitriles And Perfumery Use Of 2,2-Dimethyl-4-Phenyl Valeronitrile"). Other perfume uses of nitrile-containing derivatives which also contain phenyl moieties which are shown in U.S. Pat. No. 4,837,351 issued on Jun. 6, 1989 wherein it is indicated that the compound having the structure:

has a powerful, fresh, fruity, floral odor note accompanied by a citrus, green topnote. Furthermore, U.S. Pat. No. 3,325,369 discloses the use of cinnamonitrile as a material useful in augmenting or enhancing the aroma of perfume compositions.

In addition, a mixture of the compounds having the structures:

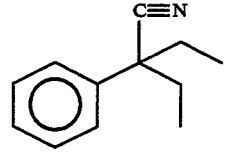

-continued
and

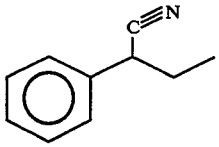

is marketed as TABACENE® by Firmenich et cie, S.A. of Geneva, Switzerland (as referred to in the Fragrance Materials Association of The United States, Inc. "Trademark And Coined Names Catalogue" on page T1). Nothing in the prior art however discloses the 1-phenyl-1-cyano-$C_5$-$C_7$ alkanes of our invention having their unexpected, unobvious and advantageous uses in perfumery.

The Romanian Patent No. 75,279 abstracted at Chemical Abstracts Volume 99:139517m, 1983, discloses the reaction sequence:

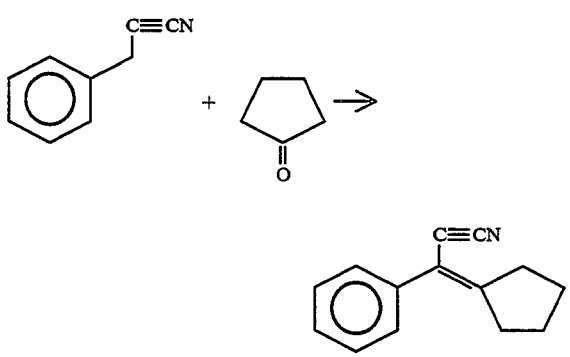

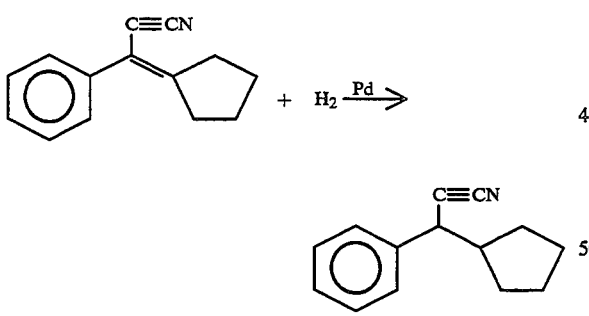

but does not set forth the unobvious, advantageous and unexpected results when using the conditions of the reaction sequence of our invention to prepare the 1-phenyl-1-cyano-$C_5$-$C_7$ alkanes of our invention having the generic structure:

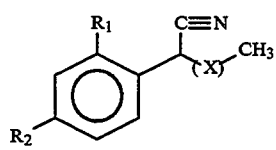

which reaction sequence is:

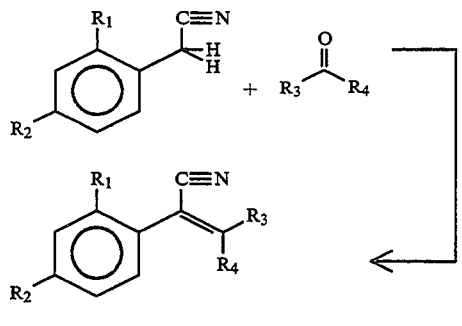

and

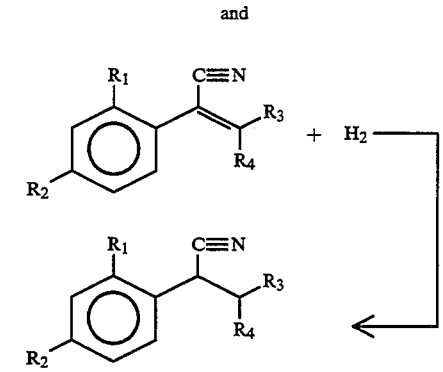

wherein $R_3$ and $R_4$ each represents hydrogen or lower alkyl with the proviso that $R_3$ and $R_4$ are not both hydrogen.

BRIEF DESCRIPTION OF THE DRAWINGS

FIG. 1 represents a cut-away side elevation view of apparatus used in forming perfumed polymers which contain imbedded in the interstices thereof certain 1-phenyl-1-cyano-$C_5$-$C_7$ alkanes of our invention including those defined according to the structure:

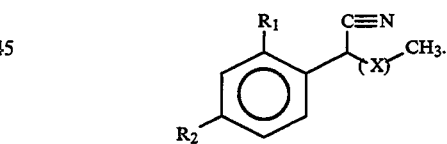

FIG. 2 is a front view of the apparatus of FIG. 1 looking in the direction of the arrows.

FIG. 3 is the GLC profile of the reaction product of Example I(A) containing the compound having the structure:

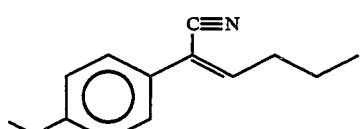

(Conditions: 30M. methyl silicone column programmed from 100°–270° C. at 8° C. per minute).

FIG. 4 is the NMR spectrum for the compound having the structure:

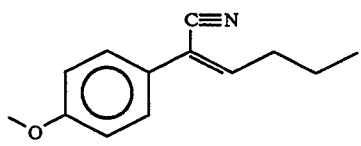

prepared according to Example I(A).

FIGS. 4A, 4B, 4C and 4D are enlargements of sections "A", "B", "C" and "D", respectively, of the NMR spectrum of FIG. 4.

Figure 5:
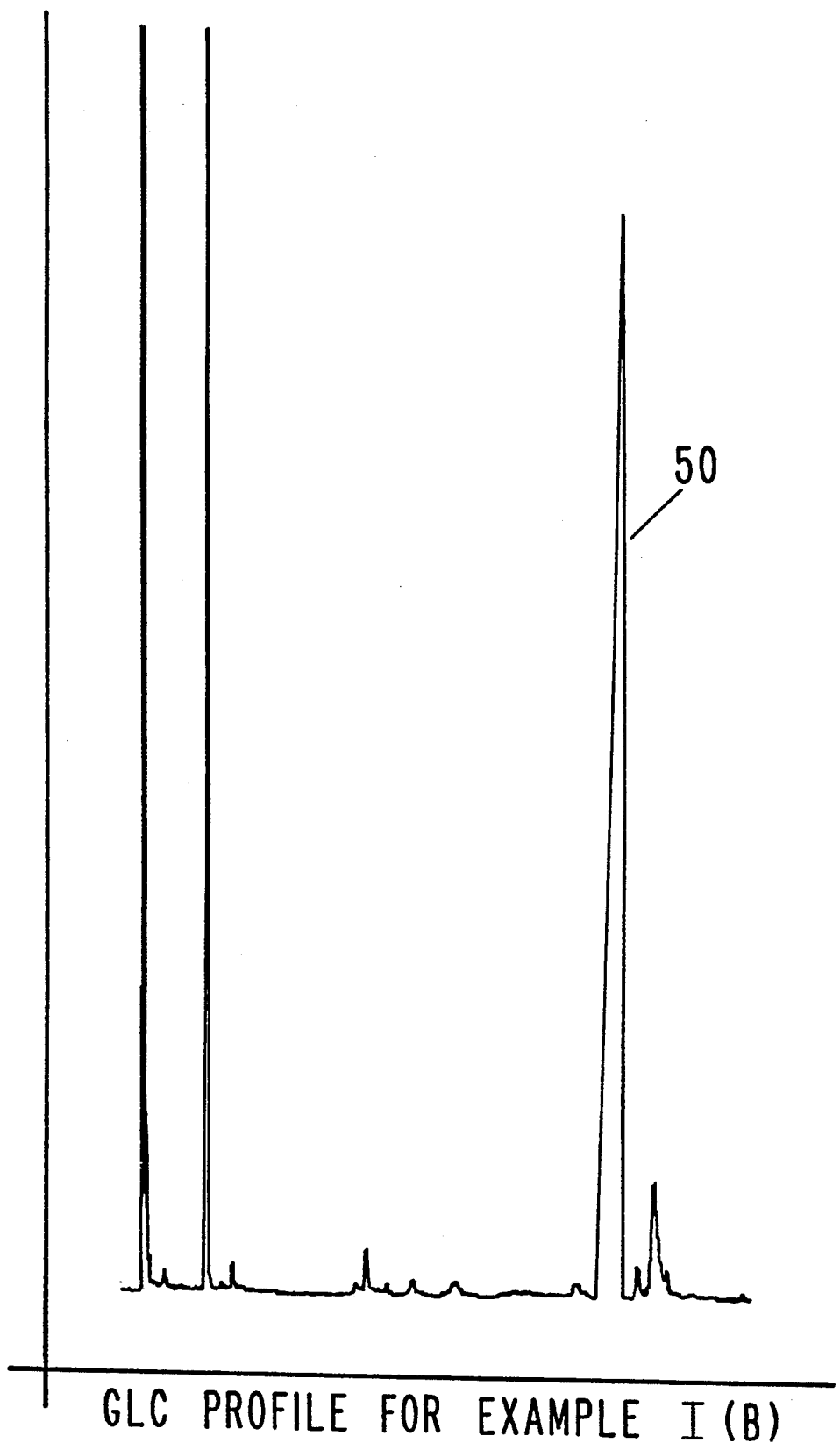

FIG. 5 is the GLC profile for the reaction product of Example I(B) containing the compound having the structure:

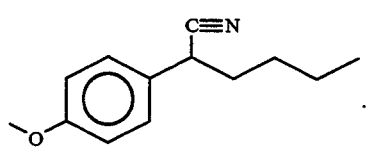

FIG. 6 is the NMR spectrum for the compound having the structure:

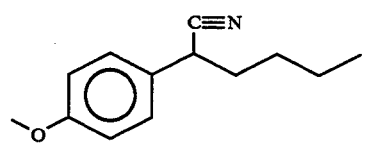

prepared according to Example I(B).

FIGS. 6A, 6B and 6C are enlargements of sections "A", "B" and "C" of the NMR spectrum of FIG. 6.

Figure 7:
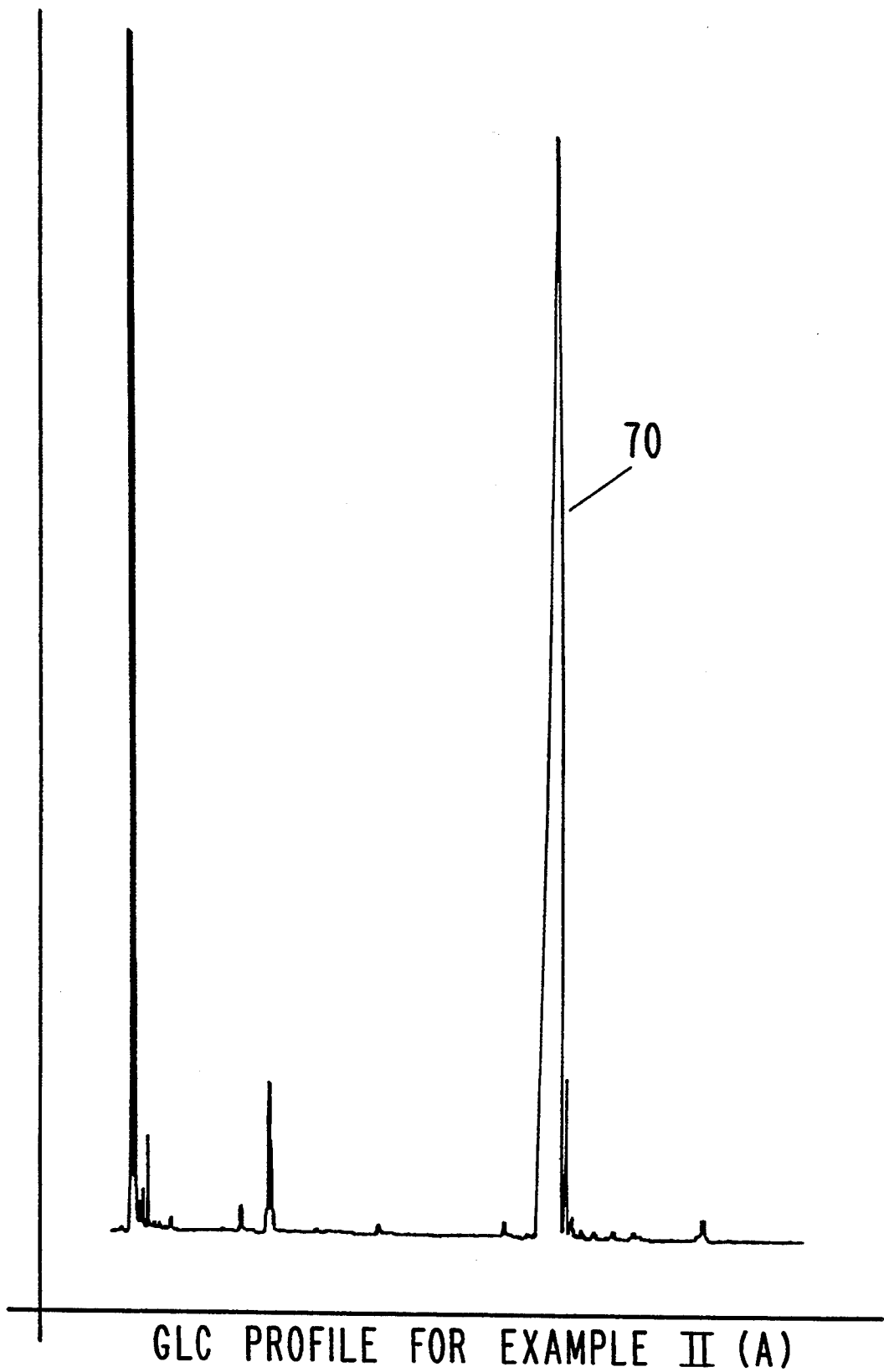

FIG. 7 is the GLC profile of the reaction product of Example II(A) containing the compound having the structure:

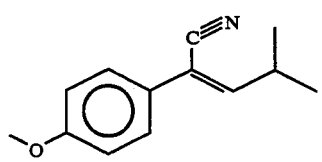

(Condtions: 0V-1 column programmed from 100°–220° C. at 8° C. per minute).

FIG. 8 is the NMR spectrum for the compound having the structure:

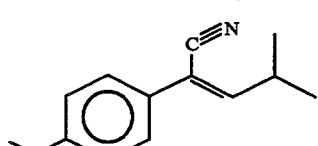

prepared according to Example II(A).

FIGS. 8A, 8B, 8C and 8D are enlargements of sections "A", "B", "C" and "D", respectively, of the NMR spectrum of FIG. 8.

Figure 9:
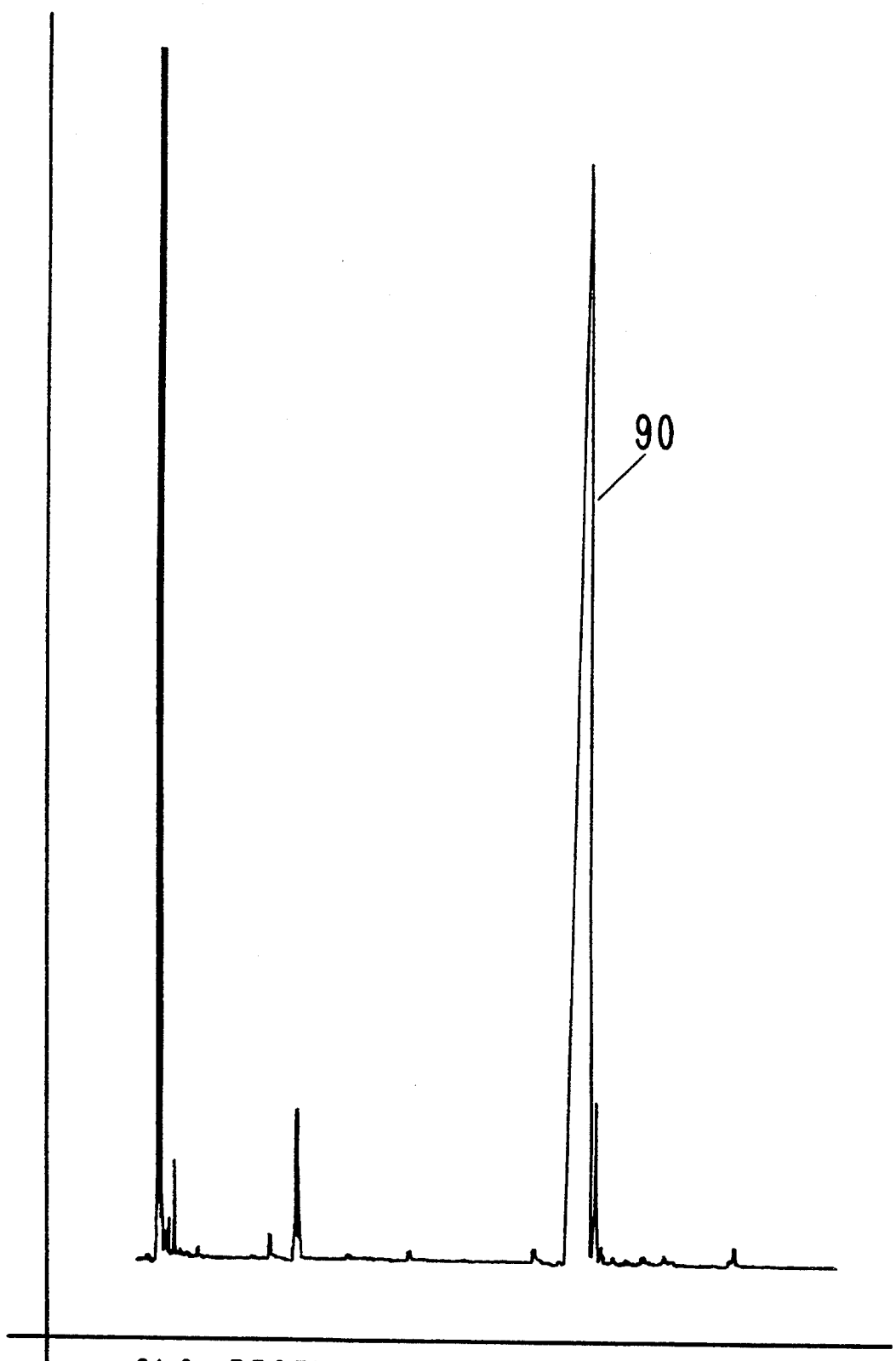

FIG. 9 is the GLC profile for the reaction product of Example II(B) containing the compound having the structure:

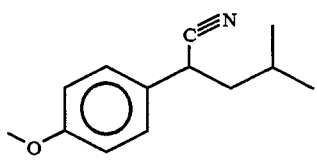

FIG. 10 is the NMR spectrum for the compound having the structure:

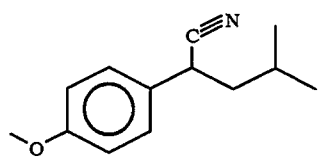

prepared according to Example II(B).

FIGS. 10A, 10B and 10C are enlargements of section "A", "B" and "C" of the NMR spectrum of FIG. 10.

Figure 11:
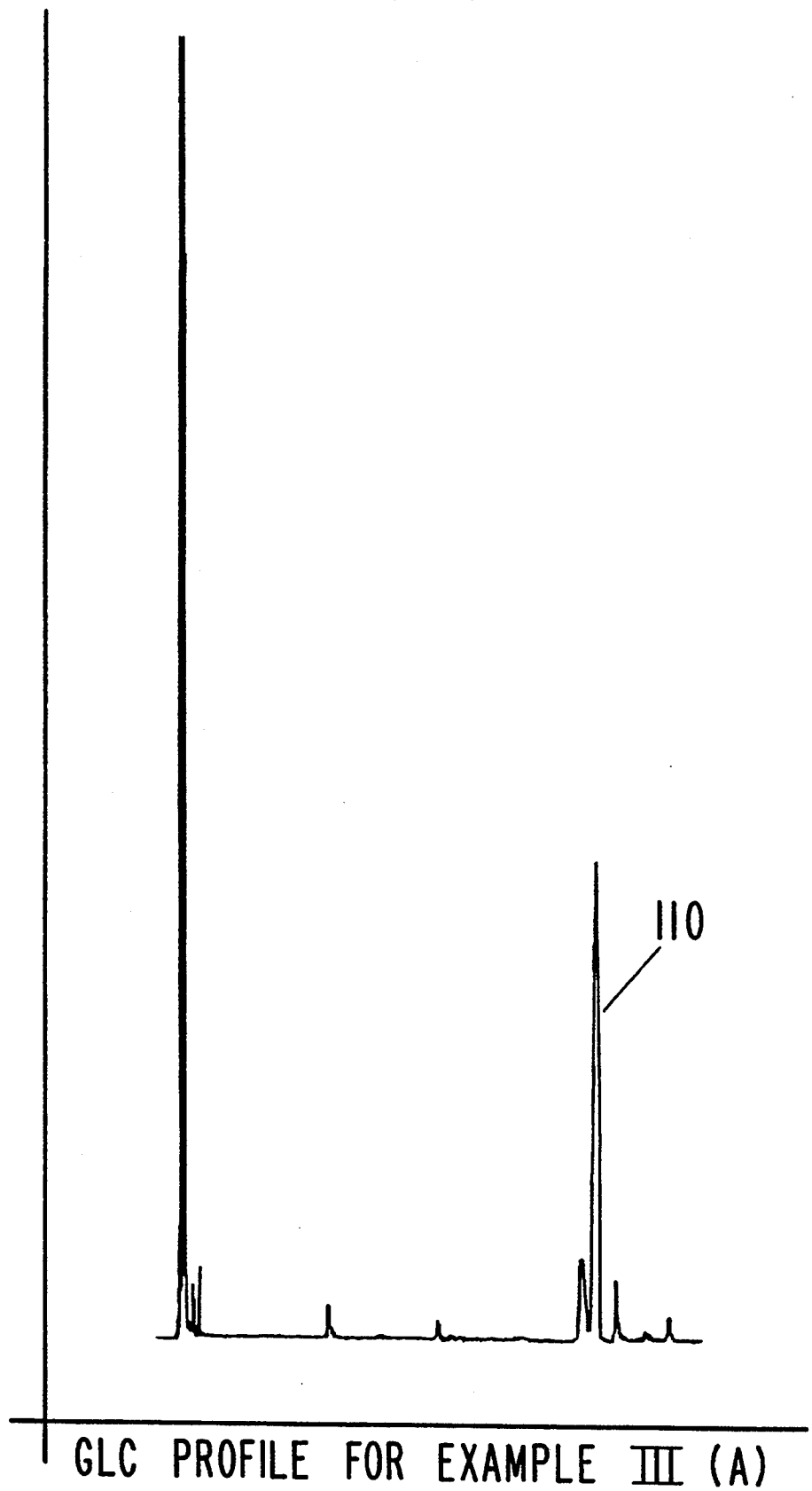

FIG. 11 is the GLC profile for the reaction product of Example III(A) containing the compound having the structure:

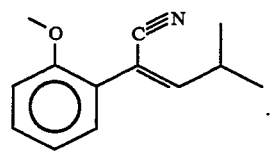

FIG. 12 is the NMR spectrum for the compound having the structure:

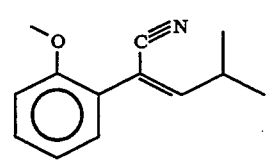

prepared according to Example III(A).

FIGS. 12A, 12B, 12C and 12D are enlargements of sections "A", "B" "C" and "D" of the NMR spectrum of FIG. 12.

Figure 13:
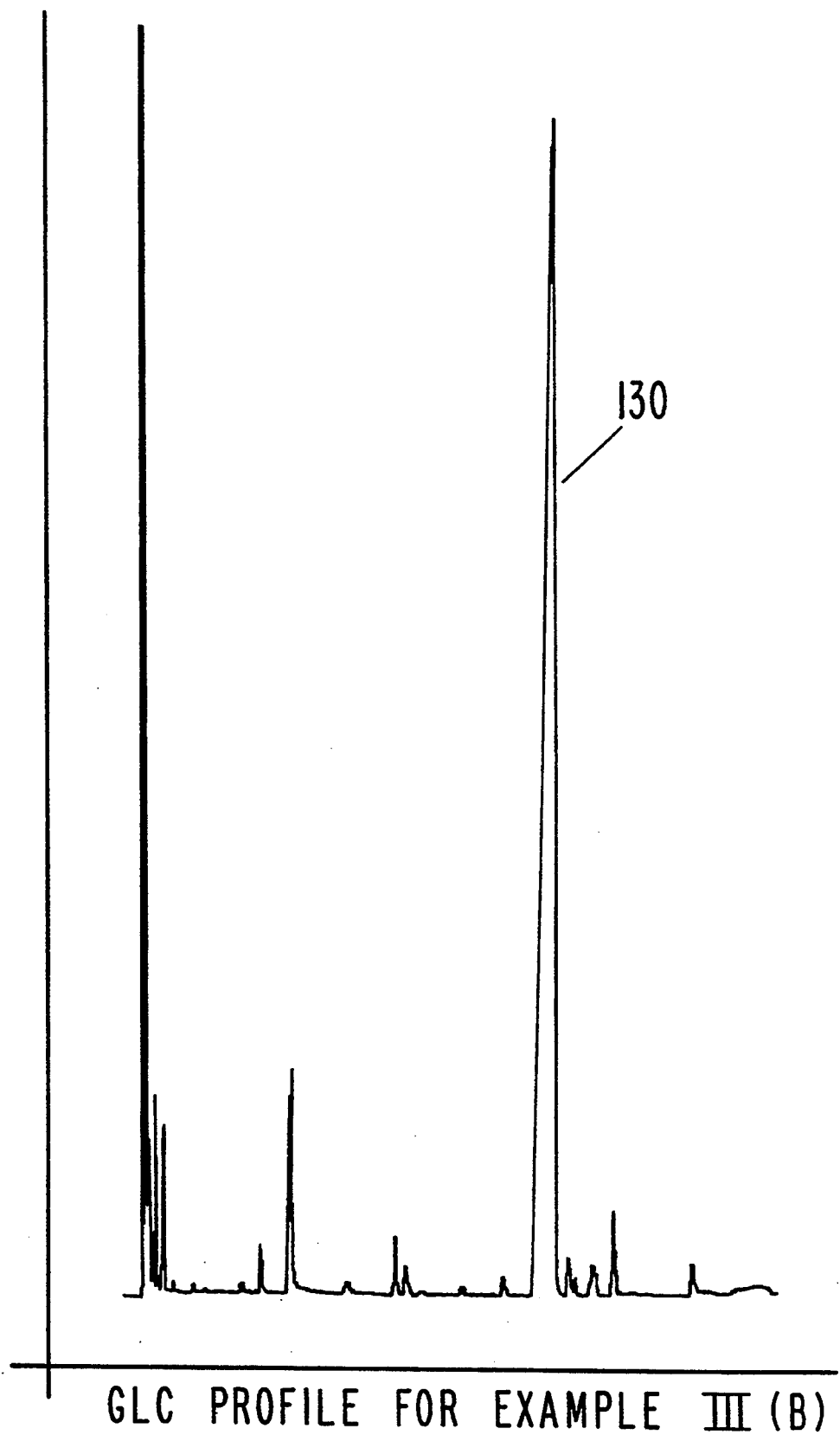

FIG. 13 is the GLC profile for the reaction product of Example III(B) containing the compound having the structure:

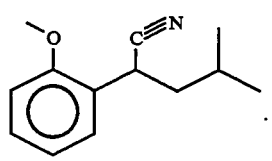

FIG. 14 is the NMR spectrum for the compound having the structure:

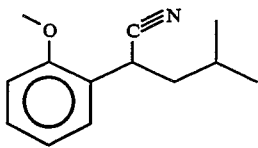

prepared according to Example III(B).

FIGS. 14A, 14B and 14C are enlargements of sections "A", "B" and "C" of the NMR spectrum of FIG. 14.

Figure 15:
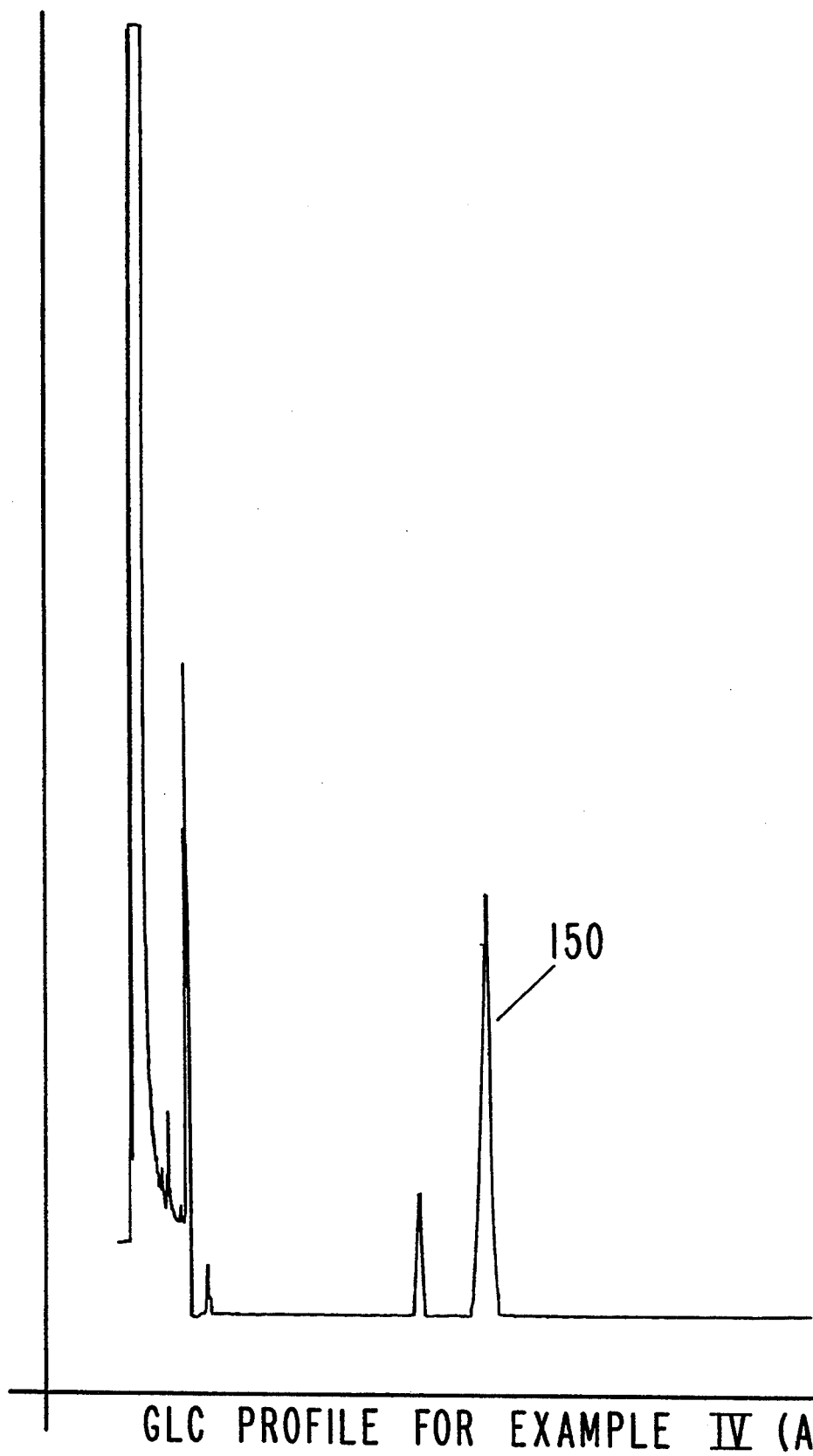

FIG. 15 is the GLC profile for the reaction product of Example IV containing the compound having the structure:

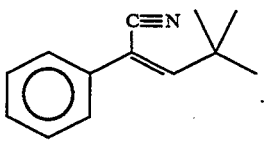

FIG. 16 is the NMR spectrum for the compound having the structure:

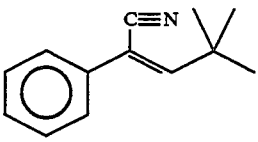

prepared according to Example IV(A).

FIGS. 16A and 16B are enlargements of sections "A" and "B", respectively, of the NMR spectrum of FIG. 16.

Figure 17:
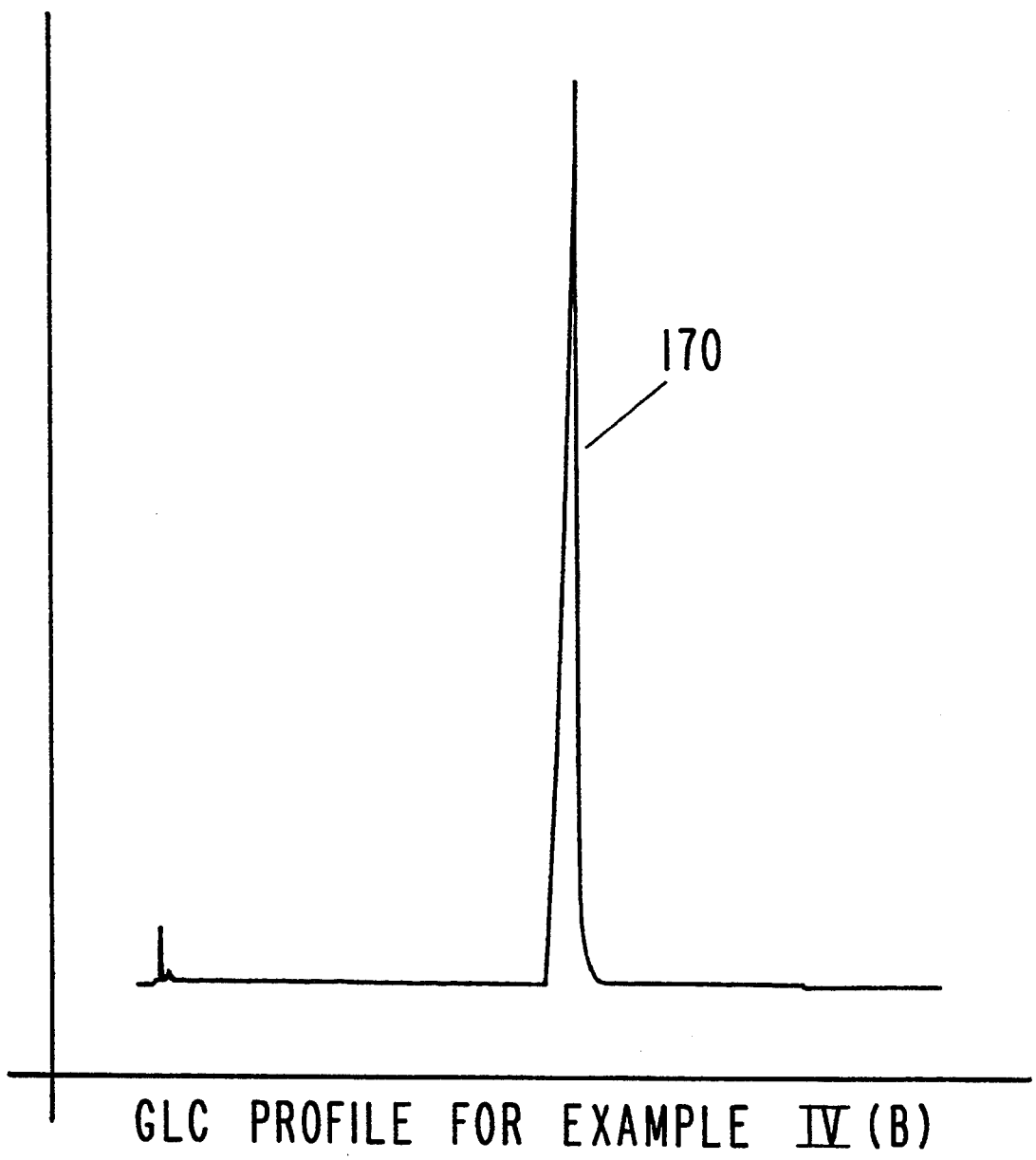

FIG. 17 is the GLC profile for the reaction product of Example IV(B) containing the compound having the structure:

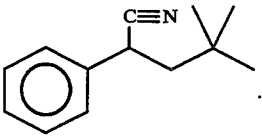

FIG. 18 is the NMR spectrum for the compound having the structure:

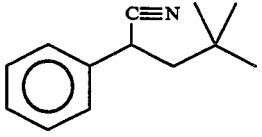

prepared according to Example IV(B).

FIGS. 18A, 18B and 18C are enlargements of sections "A", "B" and "C", respectively, of the NMR spectrum of FIG. 18.

DETAILED DESCRIPTION OF THE DRAWINGS

Referring to FIGS. 1 and 2, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 1 and 2, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the materials defined according to the generic structure:

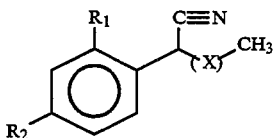

referred to hereafter as a "1-phenyl-1-cyano-$C_5$-$C_7$ alkane" of our invention and other compatible perfumes is placed. The container is closed by means of an airtight lid 228 and clamped to the container by bolts 265. A stirrer 273 traverses the lid or cover 228 in an air-tight manner and is rotatable in a suitable manner. A surrounding cylinder 212 having heating coils 212A which are supplied with electric current through cable 214 from a rheostat or control 216 is operated to maintain the temperature inside the container 212 such that the polymer in the container will be maintained in the molten or liquid state at such a temperature that the viscosity will be in the range of 90–100 sayboldt seconds. The heater 212A is operated to maintain the upper portion of the container 212 within a temperature range of, for example, 220°–270° C. in the case of low density polyethylene. The bottom portion of the container 212 is heated by means of heating coils 212A regulated through the control 220 which is connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one of the 1-phenyl-1-cyano-$C_5$-$C_7$ alkanes of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by use of the heating coil 212A. The controls 216 and 220 are connected through cables 224 and 226 to a suitable supply of electric current for supplying the power for heating purposes.

Thereafter the valve "V" is opened permitting the mass to flow outwardly through conduit 232 having a multiplicity of orifices 234 adjacent to the lower side thereof. The outer end of the conduit 232 is closed so that liquid polymer is in intimate admixture with at least one of the 1-phenyl-1-cyano-$C_5$–$C_7$ alkanes of our invention and one or more other substances if desired.

The resulting mixture will continuously drop through the orifices 234 downwardly from the conduit 232. During this time, the temperature of the polymer intimately admixed with the perfumery substance in the container 212 is accurately controlled so that a temperature in the range of from about 240°–250° C. for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is at least one of the 1-phenyl-1-cyano-$C_5$–$C_7$ alkanes of our invention through the orifices 234 at a rate which will insure the formation of droplets 236 which will fall downwardly onto a moving conveyor belt 238 caused to run between conveyor wheels 240 and 242 beneath conduit 232.

When the droplets 236 fall onto the conveyor 238 they form pellets 244 which harden almost instantaneously and fall off the end of the conveyor 238 into a container 245 which is advantageously filled with water or some other suitable cooling liquid to insure the rapid cooling of each of the pellets 244. The pellets 244 are then collected from the container 245 and utilized for the formation of functional products, e.g., fragranced garbage bags and the like. Belt 238 is precooled by means of cooling water entrapped in a sponge 256, the cooling water being inserted by reference numeral 254 contained in container 250 having side walls 248. As belt 238 moves it impinges upon sponge 256 and is thereby cooled.

Referring to FIG. 3, FIG. 3 is the GLC profile of the reaction product of Example I(A). The peak indicated by reference numeral 30 is the peak for the compound having the structure:

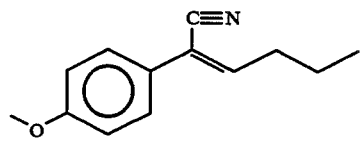

FIG. 5 is the GLC profile for the reaction product of Example I(B). The peak indicated by reference numeral 50 is the peak for the compound having the structure:

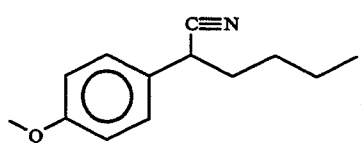

FIG. 7 is the GLC profile for the reaction product of Example II(A). The peak indicated by reference numeral 70 is the peak for the compound having the structure:

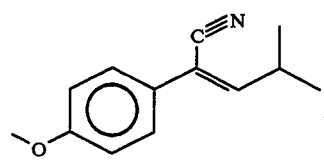

FIG. 9 is the GLC profile for the reaction product of Example II(B). The peak indicated by reference numeral 90 is the peak for the compound having the structure:

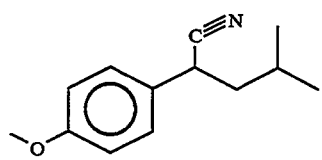

FIG. 11 is the GLC profile for the reaction product of Example III(A). The peak indicated by reference numeral 110 is the peak for the compound having the structure:

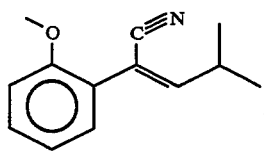

FIG. 13 is the GLC profile for the reaction product of Example III(B). The peak indicated by reference numeral 130 is the peak for the compound having the structure:

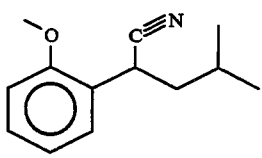

FIG. 15 is the GLC profile for the reaction product of Example IV(A). The peak indicated by reference numeral 150 is the peak for the compound having the structure:

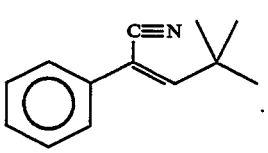

FIG. 17 is the GLC product for the reaction product of Example IV(B). The peak indicated by reference numeral 170 is the peak for the compound having the structure:

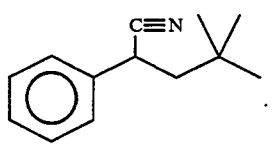

THE INVENTION

The present invention provides 1-phenyl-1-cyano-C₅–C₇ alkanes defined according to the structure:

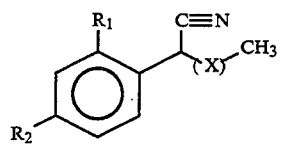

wherein $R_1$ and $R_2$ each represents hydrogen or methoxy with the proviso that when $R_1$ is methoxy, $R_2$ is hydrogen and when $R_2$ is methoxy, $R_1$ is hydrogen; and wherein X represents $C_3$–$C_5$ straight chain or branched chain alkylene in augmenting or enhancing or imparting aroma to or in perfume compositions, perfumed articles and colognes.

The compounds having the structures:

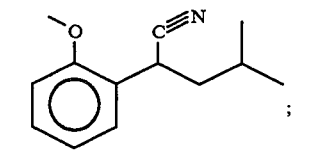

;

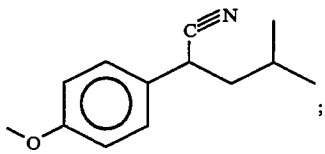

;

and

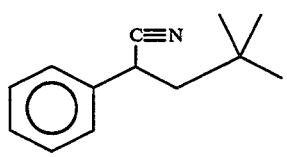

are novel compounds.

The compounds defined according to the generic structure:

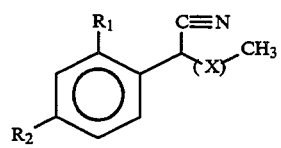

have uses in augmenting or enhancing the aroma of perfume compositions, colognes and perfumed articles including but not limited to perfumed polymers, cosmetic powders, anionc, cationic, nonionic or zwitterionic detergents, fabric softener compositions, fabric softener articles including drier-added fabric softener articles, (e.g., BOUNCE® marketed by the Procter & Gamble Company of Cincinnati, Ohio).

The compounds shown by the generic structure:

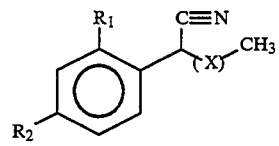

are hereinafter referred to as the 1-phenyl-1-cyano-C₅–C₇ alkanes of our invention. The 1-phenyl-1-cyano-C₅–C₇ alkanes of our invention are capable of imparting, augmenting or enhancing floral, rose, muguet, herbal, green, fruity, pineapple-like, salicylate, basil, sweet, living orange flower, almond, cherry, woody, cigar box-like, ambergris, animalic, honey-like, musky, balsamic, cedarwood and sage-like aromas with sweet, green, floral, muguet, rose, salicylate, anethole-like, carvone-like, costus and almondy undertones and with sweet, woody, fruity, wine-like, green, salicylate, animalic, honey-like, floral, rose, cabreuva oil-like and bois-de-rose topnotes and with a cooling effect on the skin on dry out to perfume compositions, colognes and perfumed articles including soaps, bleaches, anionic, cationic, nonionic or zwitterionic detergents, fabric softener articles and other perfumed articles.

The process of our invention involves first reacting a benzyl cyanide having the structure:

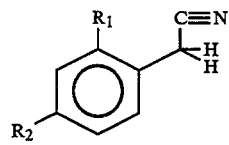

with an aldehyde or ketone having the structure:

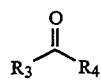

wherein $R_3$ and $R_4$ are the same or different hydrogen or lower alkyl with the proviso that $R_3$ and $R_4$ are not both hydrogen according to the reaction:

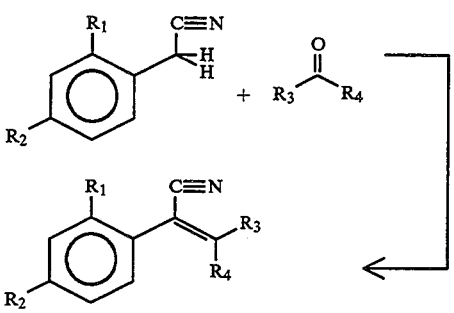

The resulting product having the structure:

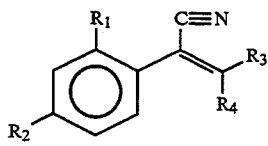

is then hydrogenated using a supported palladium catalyst, (palladium on carbon) according to the reaction:

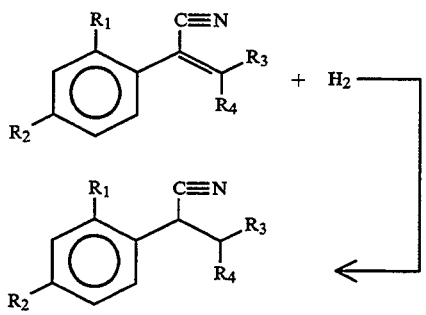

thereby forming the products defined according to the structure:

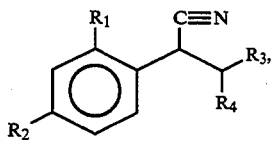

also shown by the structure:

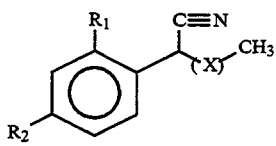

the 1-phenyl-1-cyano-$C_5$–$C_7$ alkanes of our invention.

In carrying out the reaction:

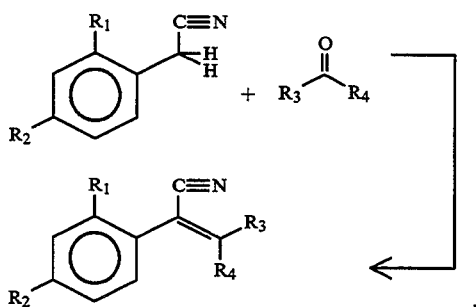

this reaction is carried out at 35°–90° C. using an alcoholic nonaqueous alkali metal hydroxide catalyst. The alcohol can be either methyl alcohol or ethyl alcohol. The alkali metal hydroxide may be either potassium hydroxide or sodium hydroxide. The mole ratio of aldehyde or ketone:benzyl cyanide derivative may vary from about 0.5:1 up to about 1:0.5 with a preferred mole ratio of 1:1. The ratio of alkali metal hydroxide:alcohol may vary from about 40 grams per liter up to about 120 grams per liter. The ratio of compound having the structure:

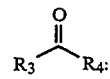

alcohol (e.g., methyl alcohol or ethyl alcohol) may vary from about 2 moles per liter up to about 6 moles per liter. The reaction time may vary from about 5 hours up to about 30 hours.

In carrying out the reaction:

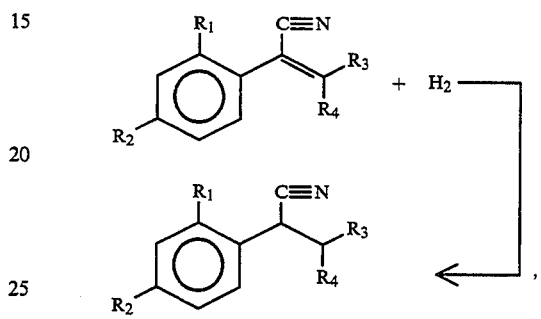

this reaction is carried out from about 80° C. up to about 100° C. at from about 300 up to about 600 psig (pounds per square inch gauge). The reaction is carried out using a palladium on carbon (supported) catalyst with the amount of palladium on carbon varying from about 3% up to about 10% palladium, with a preferred palladium percentage being 5%.

At the end of the reaction, the reaction mass is filtered and fractionally distilled on a fractional distillation column.

Again, referring to the reaction:

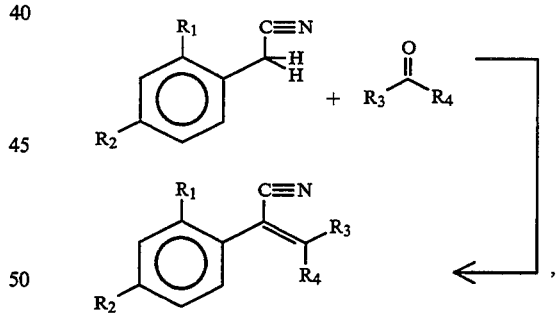

at the end of the reaction, the reaction mass is quenched with a weak acid such as acetic acid, and is then washed with water. The reaction mass is then fractionally distilled on a fractional distillation column prior to the hydrogenation reaction.

The following table sets forth the perfumery properties of the various compositions of matter defined according to the generic structure:

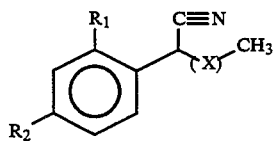

so useful in perfumery of our invention.

TABLE I

| Description of Composition | Perfumery Properties |
|---|---|
| The compound having the structure: 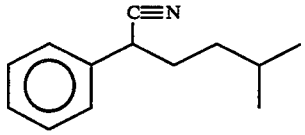 | A green, floral, "salicylate" aroma, having green, floral and fruity undertones with a "cooling" effect on the skin on dry-out. |
| The compound having the structure: 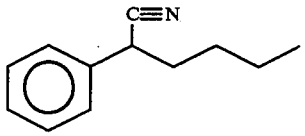 | A floral (rose/muguet), green, fruity (pineapple), "salicylate" aroma with floral (muguet), green, "salicylate", anethole-like and carvone-like undertones. |
| The compound having the structure: 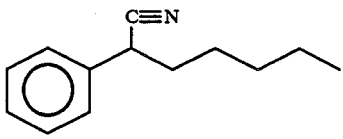 | A basil, "salicylate" aroma with fruity, wine-like topnotes. |
| The compound having the structure: 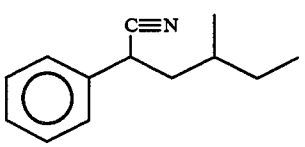 | A sweet, "salicylate" aroma with "salicylate", floral undertones. |
| The compound having the structure: 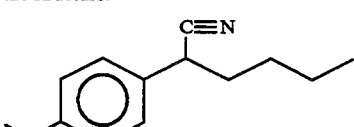 | A sweet, green, "salicylate" herbal, floral, living orange flower aroma with green, "salicylate" topnotes. |
| The compound having the structure: 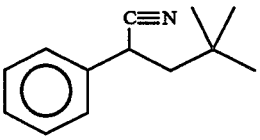 prepared according to Example I(B), bulked distillation Fractions 2–7. | An intense almond, cherry aroma with costus, sweet, almondy undertones. |
| The compound having the structure: 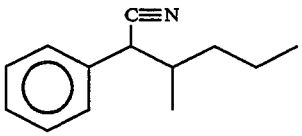 prepared according to Example IV(B), bulked distillation Fractions 5–10. | A green, woody, cigar-box like, "salicylate", ambergris aroma with green, woody topnotes. |
| The compound having the structure: | A sweet, "salicylate" aroma with sweet, |

TABLE I-continued

| Description of Composition | Perfumery Properties |
|---|---|
| 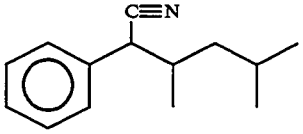 | green, "salicylate" topnotes. |
| The compound having the structure: 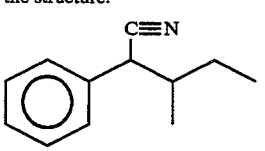 | A sweet, animalic, honey-like, floral, rose, musky, balsamic aroma with sweet, animalic, honey-like, floral, rose topnotes. |
| The compound having the structure: 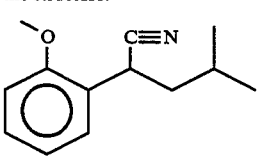 | A sweet, animalic, honey-like, green, floral (rose) aroma with-floral (rose), sweet, animalic, honey-like, and green topnotes. |
| The compound having the structure: 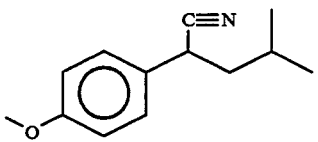 prepared according to Example III(B), bulked distillation Fractions 7 and 8. | A sweet, cedarwood aroma with sweet, cabreuva oil and bois-de-rose topnotes. |
| The compound having the structure: prepared according to Example II(B), bulked distillation Fractions 6–12. | A sage-like aroma with "salicylate" undertones. |

The 1-phenyl-1-cyano-$C_5$–$C_7$ alkanes of our invention as well as mixtures thereof and one or more auxiliary perfume ingredients including, for example, hydrocarbons, alcohols, ketones, aldehydes, nitriles (other than the nitriles of our invention), esters, lactones, ethers, hydrocarbons, synthetic essential oils and natural essential oils may be admixed so that the combined odors of the individual components produce a pleasant and desired fragrance particularly and preferably in the "floral fragrance" area. Such perfume compositions usually contain (a) the main note or the "bouquet" or foundation stone of the composition; (b) modifiers which round off and accompany the main note; (c) fixatives which include odorous substances which lend a particular note to the perfume through out all stages of evaporation and substances which retard evaporation; and (d) topnotes which are usually low-boiling, fresh smelling materials.

In perfume compositions it is the individual components which contribute to their particular olfactory characteristics however, the overall sensory effect of the perfume composition will be at least the sum total of the effects of each of the ingredients. Thus, at least one of the 1-phenyl-1-cyano-$C_5$–$C_7$ alkanes of our invention can be used to alter, modify or enhance the aroma characteristics of a perfume composition, for example, by utilizing or moderating the olfactory reaction contributed by another ingredient in the composition.

The amount of at least one of the 1-phenyl-1-cyano-$C_5$–$C_7$ alkanes of our invention which will be effective in perfume compositions as well as in perfumed articles and colognes depends upon many factors including the other ingredients, their amounts and the effects which are desired. It has been found that perfume compositions containing as little as 0.05% of at least one of the 1-phenyl-1-cyano-$C_5$–$C_7$ alkanes of our invention can be used to impart, augment or enhance floral, rose, muguet, herbal, green, fruity, pineapple-like, salicylate, basil, sweet, living orange flower, almond, cherry, woody, cigar box-like, ambergris, animalic, honey-like, musky, balsamic, cedarwood and sage-like aromas with sweet, green, floral, muguet, rose, salicylate, anethole-like, carvone-like, costus and almondy undertones and with with sweet, woody, fruity, wine-like, green, salicylate, animalic, honey-like, floral, rose, cabreuva oil-like and bois-de-rose topnotes to soaps, cosmetics, detergents (including anionic, cationic, nonionic or zwitterionic solid or liquid detergents) or other products. Furthermore, when the 1-phenyl-1-cyano-$C_5$–$C_7$ alkanes of our invention are used in a perfume, cologne or perfumed article and the resulting product is applied to the skin of a person, a pleasant "cooling" effect will be forthcoming on use of the perfume, cologne or perfumed article by said person.

The amount employed can range up to 70% and even higher of the fragrance components (e.g., 100%) and will depend on considerations of cost, nature of the end product, the effects desired on the finished product and the particular fragrance sought.

At least one of the 1-phenyl-1-cyano-$C_5$–$C_7$ alkanes of our invention are useful (taken alone or taken together with other ingredients in perfume compositions) in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders, such as talcs, dusting powders, face powders and the like.

As little as 0.7% of at least one of the 1-phenyl-1-cyano-$C_5$–$C_7$ alkanes of our invention or mixtures thereof will suffice to impart, enhance or augment an intense and substantive floral, rose, muguet, herbal, green, fruity, pineapple-like, salicylate, basil, sweet, living orange flower, almond, cherry, woody, cigar box-like, ambergris, animalic, honey-like, musky, balsamic, cedarwood and sage-like aroma with sweet, green, floral, muguet, rose, salicylate, anethole-like, carvone-like, costus and almondy undertones and with sweet, woody, fruity, wine-like, green, salicylate, animalic, honey-like, floral, rose, cabreuva oil-like and bois-de-rose topnotes to floral perfume formulations. Generally, no more than 5% of at least one of the 1-phenyl-1-cyano-$C_5$–$C_7$ alkanes of our invention or mixtures thereof based on the ultimate end product is required to be used "as is" or in the perfume composition.

Furthermore, as little as 0.25% of at least one of the 1-Phenyl-1-cyano-$C_5$–$C_7$ alkanes of our invention or mixtures thereof will suffice to impart such aroma to perfumed articles per se, whether in the presence of other perfume materials or whether used by themselves. Thus, the range of use of at least one of the 1-phenyl-1-cyano-$C_5$–$C_7$ alkanes of our invention or mixtures thereof in perfumed articles may vary from about 0.25% up to about 5% by weight based on the total weight of the perfumed article.

In addition, the perfume composition or fragrance compositions of our invention can contain a vehicle or carrier for at least one of the 1-phenyl-1-cyano-$C_5$–$C_7$ alkanes of our invention. The vehicle can be a liquid such as a non-toxic alcohol, e.g., ethanol, a non-toxic glycol, e.g., propylene glycol, or the like. The carrier can also be an adsorbent solid such as a gum (e.g., gum arabic) or components for encapsulating the composition as by means of coacervation (such as gelatin).

It will thus be apparent that at least one of the 1-phenyl-1-cyano-$C_5$–$C_7$ alkanes of our invention can be utilized to alter, modify or enhance the aroma of perfume compositions, colognes or perfumed articles.

Furthermore, a number of processes known in the art and set forth, for example, in U.S. Pat. No. 5,143,899 issued on Sep. 1, 1992 the specification for which is incorporated by reference herein may be used in order to produce a thickened, highly viscous hypochlorite bleaching or sterilizing solution, whereby the desired aroma profiles are imparted to the articles treated with such hypochlorite solutions. Specifically, the disclosure as set forth at columns 12, 13, 14, 15, 16, 17 and 18 of said U.S. Pat. No. 5,143,899 which is incorporated by reference herein.

The following Examples I, II, III and IV serve to illustrate processes for preparing the 1-phenyl-1-cyano-$C_5$–$C_7$ alkanes of our invention.

Examples following Example IV in general serve to illustrate the organoleptic utilities of the 1-phenyl-1-cyano-$C_5$–$C_7$ alkanes of our invention.

In general, the following examples serve to illustrate specific embodiments of our invention. It will be understood that these examples are illustrative and that the invention is to be considered restricted thereto only as indicated in the appended claims.

All parts and percentages given herein are by weight unless otherwise specified.

EXAMPLE I

PREPARATION OF 2[4'-METHOXYPHENYL]HEXANENITRILE

EXAMPLE I (A)

Reaction:

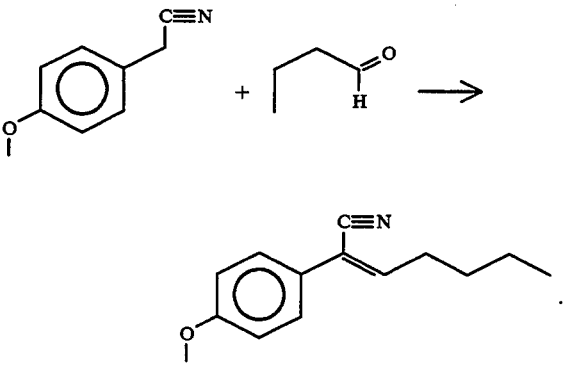

Into a 3 liter reaction flask (3 liter) is added a mixture of 60 grams of potassium hydroxide and 500 ml anhydrous methyl alcohol. The resulting mixture is cooled to 37° C. Over a period of one hour while maintaining the reaction mass at 40°–45° C., 200 grams of butyraldehyde is added to the reaction mass.

While the reaction mass is maintained at 45°–50° C. 250 grams of the compound having the structure:

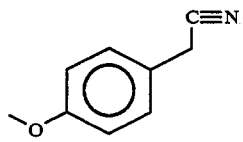

is added to the reaction mass with stirring. The reaction mass is maintained at 50° C. for a period of five hours.

The reaction mass is then fractionally distilled to yield the compound having the structure:

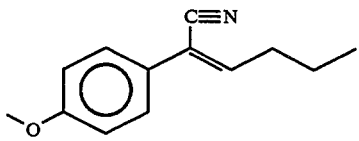

EXAMPLE I(B)

Reaction:

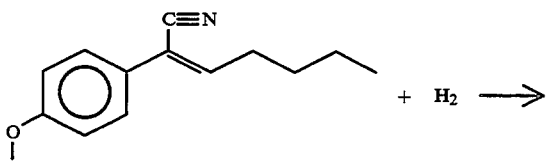

The compound having the structure:

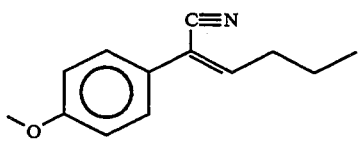

is admixed with a 5% palladium on carbon catalyst and placed in an autoclave fitted with a hydrogen feed tube. The autoclave is operated at 400 psig pressure and at a temperature of 80° C. The autoclave is operated for a period of one hour.

The autoclave is then cooled and opened and the resulting product is fractionally distilled yielding the following fractions:

| Fraction No. | Vapor Temp. (°C.) | Liquid Temp. (°C.) | Vacuum mm/Hg. Pressure |
|---|---|---|---|
| 1 | 142/ | 180/ | 2.1 |
| 2 | 166 | 185 | 4.0 |
| 3 | 166 | 186 | 3.9 |
| 4 | 167 | 189 | 3.0 |
| 5 | 167 | 194 | 2.9 |
| 6 | 167 | 200 | 3.5 |
| 7 | 167 | 215 | 4.4 |
| 8 | 162 | 215 | 4.2. |

The resulting product has the structure:

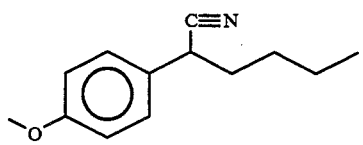

as confirmed by NMR, IR and mass spectral analysis.

EXAMPLE II

PREPARATION OF 2[4′-METHOXYPHENYL]-4-METHYL-PENTANENITRILE

EXAMPLE II (A)

Reaction:

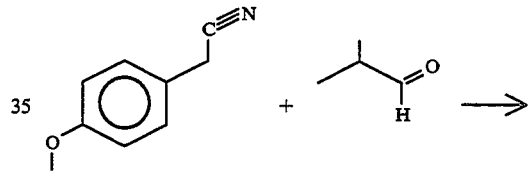

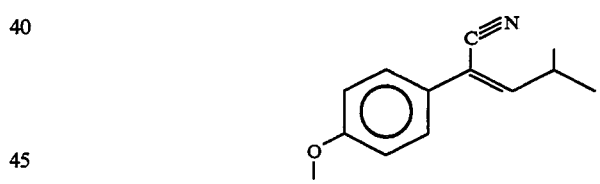

Into a 3 liter reaction vessel equipped with stirrer, thermometer, reflux condenser and heating mantle is placed a mixture of 60 grams of solid potassium hydroxide and 500 ml of methyl alcohol anhydrous. The resulting mixture is cooled to 30° C. While maintaining the resulting mixture at 30°–40° C., 200 grams of isobutyraldehyde is added to the reaction mass over a period of one hour. While maintaining the reaction mass at 40°–45° C. with stirring, 250 grams of the compound having the structure:

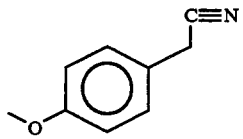

is added to the reaction mass over a period of two hours. The reaction mass is then maintained at 46° C. for an additional period of six hours. At the end of the reaction, the reaction mass is cooled and quenched with an equal volume of acetic acid. The organic phase is separated from the aqueous phase and the organic phase is fractionally distilled to yield the compound having the structure:

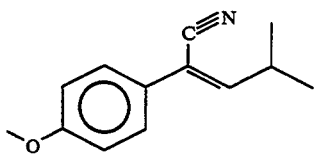

as confirmed by NMR, IR and mass spectral analysis.

EXAMPLE II(B)

Reaction:

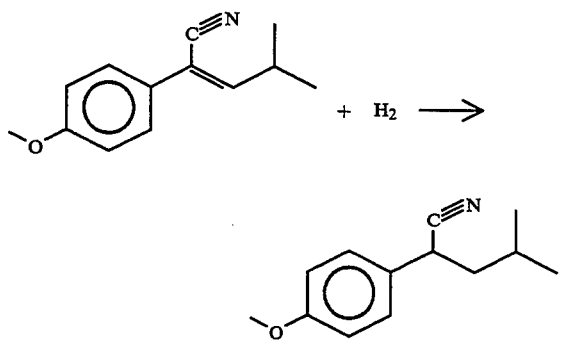

Into a 500 ml autoclave is placed the compound having the structure:

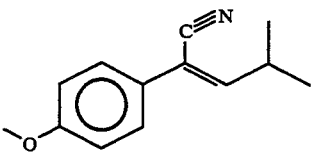

together with a 5% palladium on carbon catalyst. The autoclave is fitted with a hydrogen feed tube. The autoclave is closed and operated at 400 psig and at a temperature of 75° C. for a period of one hour. At the end of the one hour period, the autoclave is cooled and opened. The contents are filtered and the fitrate is then fractionally distilled yielding the following fractions:

| Fraction No. | Vapor Temp. (°C.) | Liquid Temp. (°C.) | Vacuum mm/Hg. Pressure |
| --- | --- | --- | --- |
| 1 | 125/ | 157/ | 2.3 |
| 2 | 147 | 158 | 2.3 |
| 3 | 146 | 158 | 2.3 |
| 4 | 147 | 159 | 2.3 |
| 5 | 148 | 159 | 2.3 |
| 6 | 150 | 161 | 3.6 |
| 7 | 156 | 166 | 5.6 |
| 8 | 156 | 168 | 5.2 |
| 9 | 152 | 160 | 2.6 |
| 10 | 150 | 158 | 2.6 |
| 11 | 154 | 162 | 2.6 |
| 12 | 149 | 160 | 2.8 |
| 13 | 150 | 185 | 3.8 |
| 14 | 132 | 210 | 4.5 |

Fractions 6–12 are bulked for perfumery.

Fractions 6–12 are the compound having the structure:

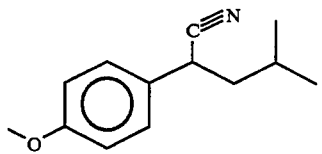

as confirmed by NMR, IR and mass spectral analysis.

EXAMPLE III

PREPARATION OF 2[2'-METHOXYPHENYL]-4-METHYLPENTANENITRILE

EXAMPLE III(A)

Reaction:

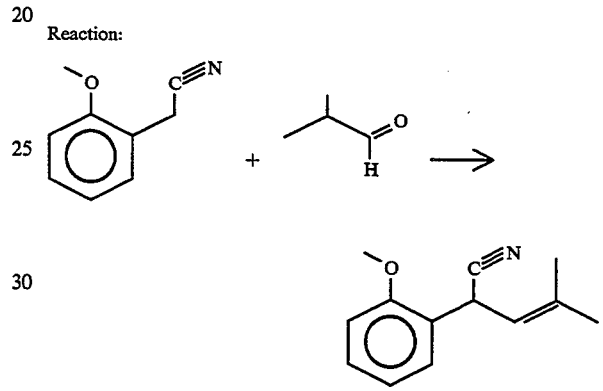

Into a 3 liter reaction vessel equipped with stirrer, thermometer, reflux condenser and heating mantle is placed a mixture of 60 grams of solid potassium hydroxide and 1 liter of anhydrous methanol. The mixture is cooled to 30° C. With stirring, over a period of one hour while maintaining the reaction mass at 42° C., 200 grams of isobutyraldehyde is added to the reaction mass. The isobutyraldehyde having the structure:

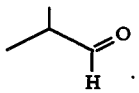

While maintaining the reaction mass at 42°–44° C., over a period of three hours, 250 grams of the compound having the structure:

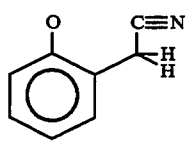

is slowly added to the reaction mass with stirring. The reaction mass is continued to be maintained at 40°–43° C. for a period of five hours. The reaction mass is then quenched with an equal volume of acetic acid and washed with two volumes of saturated aqueous sodium chloride solution. The organic phase is separated from the aqueous phase and dried over anhydrous magnesium sulfate. The resulting product is then fractionally distilled to yield the compound having the structure:

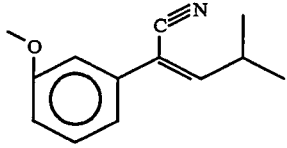

as confirmed by NMR, IR and mass spectral analysis.

EXAMPLE III(B)

Reaction:

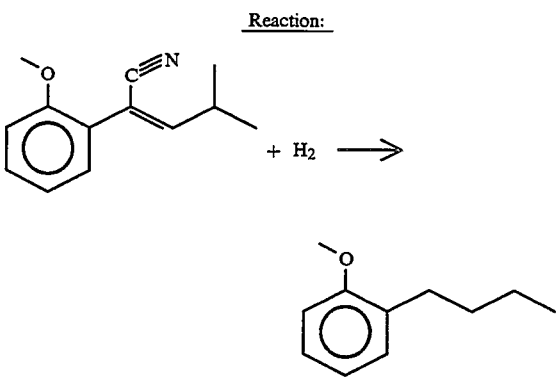

The compound having the structure:

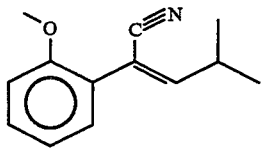

is admixed with a 5% palladium on carbon catalyst and the resulting mixture is placed in an 1 liter autoclave fitted with a hydrogenation tube. The autoclave is closed and heated to 70° C. and maintained at a pressure of 400 psig while adding hydrogen thereto. The hydrogenation takes place for a period of two hours. At the end of the two hour period, the autoclave is cooled and opened. The contents are filtered and the filtrate is distilled on a 1×10" Goodloe column yielding the following fractions:

| Fraction No. | Vapor Temp. (°C.) | Liquid Temp. (°C.) | Vacuum mm/Hg. Pressure |
|---|---|---|---|
| 1 | 92/108 | 138/139 | 1.8 |
| 2 | 132 | 143 | 2.0 |
| 3 | 138 | 148 | 3.4 |
| 4 | 138 | 148 | 2.7 |
| 5 | 138 | 148 | 2.7 |
| 6 | 138 | 148 | 3.3 |
| 7 | 138 | 148 | 3.8 |
| 8 | 138 | 148 | 3.3 |
| 9 | 143 | 155 | 4.0 |
| 10 | 128 | 200 | 4.8. |

Fractions 7 and 8 are bulked. Fractions 7 and 8 are the compound having the structure:

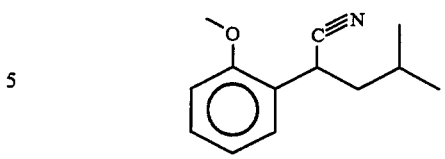

as confirmed by NMR, IR and mass spectral analysis.

EXAMPLE IV

PREPARATION OF 2-PHENYL-4,4-DIMETHYLPENTANENITRILE

EXAMPLE IV(A)

Reaction:

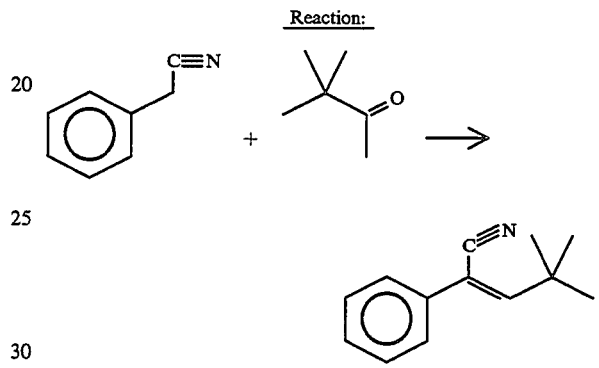

Into a 2 liter reaction vessel equipped with stirrer, thermometer, reflux condenser and heating mantle is placed a mixture containing 56 grams of solid potassium hydroxide and 1 liter of anhydrous methyl alcohol. The temperature of the mixture is maintained at 35°–40° C. While maintaining the reaction mass at 35°–40° C., over a period of one hour 500 grams of benzyl cyanide having the structure:

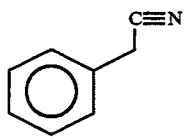

is added to the reaction mass.

Over a period of one hour while maintaining the reaction mass at 35°–40° C. 300 ml of the compound having the structure:

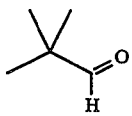

is added to the reaction mass.

The reaction mass is then stirred at 35°–40° C. for a period of nine hours.

The reaction mass is then quenched with 80 grams of acetic acid. The reaction mass is then washed with an equal volume of water. The organic phase is separated from the aqueous phase and the organic phase is fractionally distilled on a "rush over" column yielding the following fractions:

| Fraction No. | Vapor Temp. (°C.) | Liquid Temp. (°C.) | Vacuum mm/Hg. Pressure |
|---|---|---|---|
| 1 | 56/ | 79/ | 5.00 |
| 2 | 57 | 125 | 5.00 |
| 3 | 101 | 135 | 1.4 |
| 4 | 114 | 130 | 2.0 |
| 5 | 103 | 118 | 0.8 |
| 6 | 101 | 122 | 0.8. |

Fractions 4, 5 and 6 are bulked. Bulked distillation fractions 4-6 are the compound having the structure:

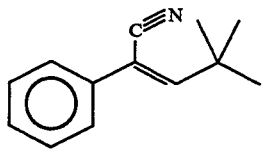

as confirmed by NMR, IR and mass spectral analysis.

EXAMPLE IV(B)

Reaction:

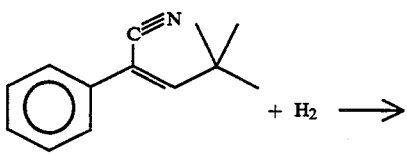

The compound having the structure:

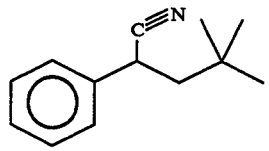

(392 grams) is admixed with 3 grams of a 5% palladium on carbon catalyst. The resulting mixture is then placed in an 1 liter autoclave equipped with a hydrogen feed tube. The autoclave is closed and pressurized with hydrogen at a pressure of 300 psig and at a temperature of 55°-60° C. The reaction takes place over a period of 0.5 hours. At the end of the reaction, the autoclave is cooled and opened and the contents are filtered. The filtrate is then fractionally distilled yielding the following fractions:

| Fraction No. | Vapor Temp. (°C.) | Liquid Temp. (°C.) | Vacuum mm/Hg. Pressure |
|---|---|---|---|
| 1 | 63/85 | 119/25 | 1/800 |
| 2 | 84 | 124 | 700 |
| 3 | 99 | 125 | 800 |
| 4 | 97 | 125 | 908 |
| 5 | 95 | 125 | 908 |
| 6 | 94 | 128 | 700 |
| 7 | 95 | 126 | 700 |
| 8 | 94 | 126 | 0.9 |
| 9 | 93 | 129 | 0.9 |
| 10 | 92 | 127 | 1.0 |
| 11 | 120 | 130 | 2.1 |
| 12 | 90 | 127 | 0.7 |
| 13 | 88 | 129 | 0.7 |
| 14 | 95 | 135 | 0.7 |
| 15 | 90 | 130 | 0.7. |

Distillation Fractions 5-10 are bulked. Distillation Fractions 5-10 are the compound having the structure:

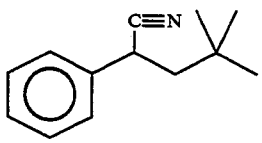

as confirmed by NMR, GLC, mass spectral and IR analyses.

EXAMPLE V

The following Chypre formulations are prepared:

| Ingredients | Example IV (A) | Example IV(B) | Example IV(C) |
|---|---|---|---|
| Musk ambrette | 40 | 40 | 40 |
| Musk ketone | 60 | 60 | 60 |
| Coumarin | 30 | 30 | 30 |
| Oil of bergamot | 150 | 150 | 150 |
| Oil of lemon | 100 | 100 | 100 |
| Methyl ionone | 50 | 50 | 50 |
| Hexyl cinnamic aldehyde | 100 | 100 | 100 |
| Hydroxycitronellal | 100 | 100 | 100 |
| Oil of lavender | 50 | 50 | 50 |
| Texas cedarwood oil | 85 | 85 | 85 |
| Virginia cedarwood oil | 30 | 30 | 30 |
| Oil of sandalwood (East Indies) | 40 | 40 | 40 |
| Eugenol | 10 | 10 | 10 |
| Benzyl acetate | 30 | 30 | 30 |
| alpha-Phenyl ethyl alcohol | 40 | 40 | 40 |
| beta-Phenyl ethyl alcohol | 30 | 30 | 30 |
| Oakmoss absolute | 30 | 30 | 30 |
| Vetiver oil Venezuela | 25 | 25 | 25 |
| The compound having the structure: 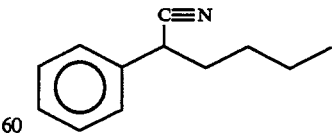 | 62 | 0 | 0 |
| The compound having the structure: 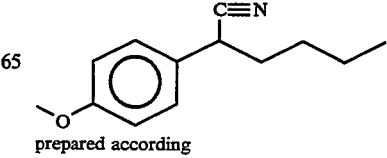 prepared according | 0 | 62 | 0 |

-continued

| Ingredients | Parts by Weight | | |
|---|---|---|---|
| | Example IV (A) | Example IV(B) | Example IV(C) |
| to Example I(B), bulked distillation Fractions 2-7. The compound having the structure: 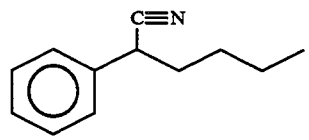 prepared according to Example IV(B), bulked distillation Fractions 5-10. | 0 | 0 | 62 |

The compound having the structure:

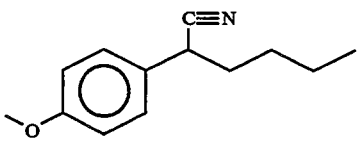

imparts to this Chypre formulation a floral, rose, muguet, green, fruity, pineapple, "salicylate" topnote profile and a floral, muguet, green, salicylate, anethole and carvone-like undertone. Accordingly, the "Chypre" formulation of Example V(A) can be described as "a Chypre aroma with floral, rose, muguet, green, fruity, pineapple, salicylate topnotes and floral, muguet, green, salicylate, anethole and carvone undertones".

The compound having the structure:

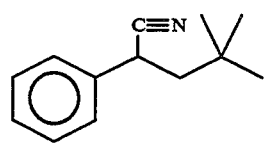

prepared according to Example I(B) bulked distillation Fractions 2-7 imparts to this Chypre formulation, almond and cherry topnotes and costus, sweet and almond undertones. Accordingly, the Chypre formulation of Example V(B) can be described as "a Chypre aroma with almond and cherry topnotes and costus, sweet and almond undertones".

The compound having the structure:

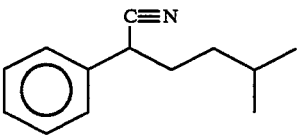

prepared according to Example IV(B), bulked distillation Fractions 5-10 imparts to this Chypre formulation green, woody, cigar-box, "salicylate", and ambergris undertones with green and woody topnotes". Accordingly, the Chypre formulation of Example V(C) can be described as "a Chypre aroma with green, woody, cigar-box like, salicylate and ambergris undertones and green and woody topnotes".

EXAMPLE VI

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 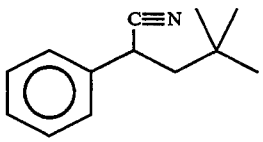 | A green, floral, "salicylate" aroma, having green, floral, fruity undertones with a "cooling" effect on the skin on dry-out. |
| The compound having the structure: 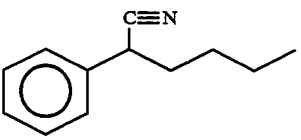 | A floral (rose/muguet), green, fruity (pineapple), "salicylate" aroma with floral (muguet), green, "salicylate", anethole-like and carvone-like undertones. |
| The compound having the structure: 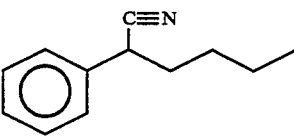 | A basil, "salicylate" aroma with fruity, wine-like topnotes. |
| The compound having the structure: 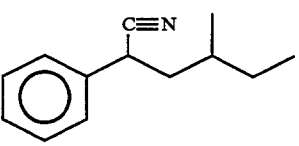 | A sweet, "salicylate" aroma with "salicylate", floral undertones. |
| The compound having the structure: 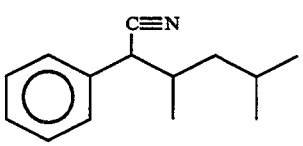 | A sweet, green, "salicylate" floral, herbal, living orange flower aroma with green, "salicylate" topnotes. |
| The compound having the structure: 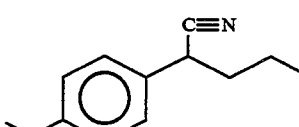 | An intense almond and cherry aroma with costus, sweet, almondy undertones. |
| prepared according to Example I(B), bulked distillation Fractions 2-7. The compound having the structure: | A green, woody, cigar-box like, |

TABLE II-continued

| Substance | Aroma Description |
|---|---|
| [structure: phenyl-CH(C≡N)-CH2-C(CH3)3] prepared according to Example IV(B), bulked distillation Fractions 5-10. | "salicylate", ambergris aroma with green, woody topnotes. |
| The compound having the structure: [phenyl-CH(C≡N)-CH(CH3)-CH2-CH3 propyl variant] | A sweet, "salicylate" aroma with sweet, green, "salicylate" topnotes. |
| The compound having the structure: [phenyl-CH(C≡N)-CH(CH3)-CH2-CH(CH3)2] | A sweet, animalic, honey-like, floral, rose, musky, balsamic aroma with sweet, animalic, honey-like, floral and rose topnotes. |
| The compound having the structure: [phenyl-CH(C≡N)-CH(CH3)-CH2CH3] | A sweet, animalic, honey-like, green, floral (rose) aroma with floral (rose), sweet, animalic, honey-like, green topnotes. |
| The compound having the structure: [2-methoxyphenyl-CH(C≡N)-CH2-CH(CH3)2] prepared according to Example III(B), bulked distillation Fractions 7 and 8. | A sweet, cedarwood aroma with sweet, cabreuva oil-like and bois-de-rose topnotes. |
| The compound having the structure: [4-methoxyphenyl-CH(C≡N)-CH2-CH(CH3)2] prepared according to Example II(B), bulked distillation Fractions 6-12. | A herbaceous, sage-like aroma with "salicylate" undertones. |
| The perfume composition of Example V(A). | A Chypre aroma with floral, rose, muguet, green, fruity, pineapple, salicylate topnotes and floral, muguet, green, salicylate, anethole and carvone undertones. |
| The perfume composition of Example V(B). | A Chypre aroma with almond and cherry topnotes and costus, sweet and almond undertones. |
| The perfume composition | A Chypre aroma with |

TABLE II-continued

| Substance | Aroma Description |
|---|---|
| of Example V(C). | green, woody, cigar box-like, salicylate and ambergris undertones and green and woody topnotes. |

EXAMPLE VII

PERFUMED LIQUID DETERGENT

Concentrated liquid detergents (Lysine salt of n-dodecyl-benzene sulfonic acid as more specifically described in U.S. Pat. No. 3,948,818 issued on Apr. 6, 1976) with aroma nuances as set forth in Table II of Example VI are prepared containing 0.10%, 0.15%, 0.20%, 0.25%, 0.30% and 0.35% of the substance set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentration of substance set forth in Table II of Example VI.

EXAMPLE VIII

PREPARATION OF COLOGNES AND HANDKERCHIEF PERFUMES

Compositions as set forth in Table II of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

PREPARATION OF SOAP COMPOSITIONS

One hundred grams of soap chips [per sample] IVORY ®, produced by the Procter & Gamble Company of Cincinnati, Ohio), are each mixed with one gram samples of substances as set forth in Table II of Example VI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VI.

EXAMPLE X

PREPARATION OF SOLID DETERGENT COMPOSITIONS

Detergents are prepared using the following ingredients according to Example I of Canadian Patent No. 1,007,948:

| | |
|---|---|
| "NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20-22}$ HAPS;
   22%—isopropyl alcohol;
   20%—antistatic agent;
   1%—of one of the substances as set forth in Table II of Example VI.

Fabric softening compositions prepared according to Example I at column 15 of U.S. Pat. No. 3,632,396 having aroma characteristics as set forth in Table II of Example VI, consist of a substrate coating having a weight of about 3 grams per 100 square inches of substrate; a first coating on the substrate coating consisting of about 1.85 grams per 100 square inches of substrate; and outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the headspace in a dryer on operation thereof in each case using said drier-added fabric softener non-woven fabrics and these aroma characteristics are described in Table II of Example VI.

EXAMPLE XII

HAIR SPRAY FORMULATIONS

The following hair spray formulation is prepared by first dissolving PVP/VA E-735 a copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid | 0.10 |
| (prepared by the Dow Corning Corporation) | |
| TWEEN ® 20 surfactant | 0.03 |
| (prepared by ICI America Corporation) | |
| One of the perfumery substances as set forth in Table II of Example VI | 0.10 |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

CONDITIONING SHAMPOOS

Nonamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

EXAMPLE XIV

Four drops of each of the substances set forth in Table II of Example VI, supra, is added separately to two grams of AROMOX ® to produce a clear premix. The clear premix is added to 200 grams of CLOROX with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example VI. Furthermore, no such characteristic "hypochlorite" aroma is retained on the hands of the individual handling such laundry in both the wet and the dry states.

EXAMPLE XV

AROMOX ® DMMC-W in various quantities is mixed with 0.1 grams of one of the substances set forth in Table II of Example VI, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite solution after addition of premix |
| --- | --- |
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example VI. Furthermore, no such characteristic "hypochlorite" aroma is retained on the hands of the individual handling such laundry in both the wet and dry states.

What is claimed is:

1. A process for imparting, augmenting or enhancing an aroma of or to a consumable material selected from the group consisting of perfume compositions, perfumed articles and colognes comprising the step of intimately admixing with a consumable material base an aroma augmenting, enhancing or imparting quantity of at least one 1-phenyl-1-cyano-$C_5$–$C_7$ alkane defined according to the structure:

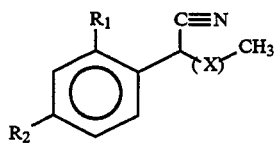

wherein $R_1$ and $R_2$ each represents hydrogen or methoxy with the proviso that when $R_1$ is methoxy, $R_2$ is hydrogen and when $R_2$ is methoxy, $R_1$ is hydrogen; and wherein X represents $C_3$–$C_5$ straight chain or branched chain alkylene.

2. The process of claim 1 wherein the 1-phenyl-1-cyano-$C_5$–$C_7$ alkane has the structure:

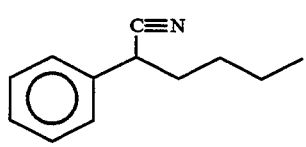

3. The process of claim 1 wherein the consumable material is a perfume composition.

4. The process of claim 1 wherein the consumable material is a perfumed article and the perfumed article is a solid or liquid anionic, cationic, nonionic or zwitterionic detergent.

5. The process of claim 1 wherein the consumable material is a perfumed article and the perfumed article is a perfumed polymer.

6. A perfumed consumable material selected from the group consisting of perfume compositions, perfumed articles, perfumed polymers and colognes comprising a consumable material base and intimately admixed therewith an aroma imparting, augmenting or enhancing quantity of at least one 1-phenyl-1-cyano-$C_5$–$C_7$ alkane defined according to the structure:

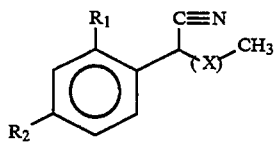

wherein $R_1$ and $R_2$ are each hydrogen or methoxy with the proviso that when $R_1$ is methoxy, $R_2$ is hydrogen and when $R_2$ is methoxy, $R_1$ is hydrogen; and wherein X is $C_3$–$C_5$ straight chain or branched chain alkylene.

7. A perfumed consumable material of claim 6 wherein the consumable material is a perfume composition and wherein the 1-phenyl-1-cyano-$C_5$–$C_7$ alkane has the structure:

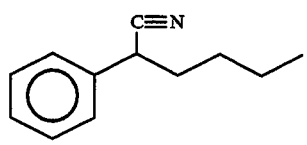

8. A perfumed consumable material of claim 6 wherein the consumable material is a cologne and comprises water, ethanol and wherein the 1-phenyl-1-cyano-$C_5$–$C_7$ alkane has the structure:

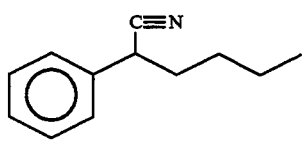

9. A perfumed consumable material of claim 6 wherein the consumable material is a microporous polymer containing in the interstices thereof an aroma imparting quantity of the 1-phenyl-1-cyano-$C_5$–$C_7$ alkane having the structure:

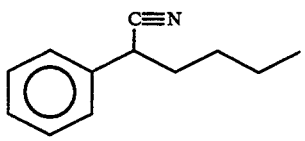

* * * * *